(12) United States Patent
Parish et al.

(10) Patent No.: US 10,507,131 B2
(45) Date of Patent: *Dec. 17, 2019

(54) METHOD AND SYSTEM FOR THERMAL AND COMPRESSION THERAPY RELATIVE TO THE PREVENTION OF DEEP VEIN THROMBOSIS

(71) Applicant: ThermoTek, Inc., Flower Mound, TX (US)

(72) Inventors: Overton L. Parish, Frisco, TX (US); Niran Balachandran, Lewisville, TX (US); Tony Quisenberry, Highland Village, TX (US)

(73) Assignee: ThermoTek, Inc., Flower Mound, TX (US)

( * ) Notice: Subject to any disclaimer, the term of this patent is extended or adjusted under 35 U.S.C. 154(b) by 526 days.

This patent is subject to a terminal disclaimer.

(21) Appl. No.: 14/812,745

(22) Filed: Jul. 29, 2015

(65) Prior Publication Data
US 2015/0328042 A1 Nov. 19, 2015

Related U.S. Application Data

(63) Continuation of application No. 11/733,709, filed on Apr. 10, 2007, now Pat. No. 9,119,705.
(Continued)

(51) Int. Cl.
*A61F 7/02* (2006.01)
*A61F 7/00* (2006.01)
(Continued)

(52) U.S. Cl.
CPC .............. *A61F 7/0085* (2013.01); *A61F 7/02* (2013.01); *A61H 1/008* (2013.01); *A61H 9/0078* (2013.01);
(Continued)

(58) Field of Classification Search
CPC .......... A61F 7/0085; A61F 7/02; A61H 9/007
See application file for complete search history.

(56) References Cited

U.S. PATENT DOCUMENTS

| 773,828 A | 11/1904 | Titus |
| 2,110,022 A | 3/1938 | Kliesrath |
| (Continued) | | |

FOREIGN PATENT DOCUMENTS

| CH | 670 541 | 6/1989 |
| DE | 35 22 127 | 1/1987 |
| (Continued) | | |

OTHER PUBLICATIONS

U.S. Appl. No. 15/227,417, filed Aug. 3, 2016, Overton et al.
(Continued)

*Primary Examiner* — Kaitlyn E Smith
*Assistant Examiner* — Yasamin Ekrami
(74) *Attorney, Agent, or Firm* — Winstead PC

(57) ABSTRACT

A DVT and temperature therapy system. A temperature therapy blanket includes a fluid bladder for delivering hot and/or cold therapy to a patient. The temperature therapy blanket may also include an air bladder for providing compression. The DVT system functions independently of the temperature therapy. This Abstract is provided to comply with rules requiring an Abstract that allows a searcher or other reader to quickly ascertain subject matter of the technical disclosure. This Abstract is submitted with the understanding that it will not be used to interpret or limit the scope or meaning of the claims. 37 CFR 1.72(b).

12 Claims, 14 Drawing Sheets

Related U.S. Application Data

(60) Provisional application No. 60/817,932, filed on Jun. 30, 2006, provisional application No. 60/791,132, filed on Apr. 11, 2006.

(51) Int. Cl.
*A61H 1/00* (2006.01)
*A61H 9/00* (2006.01)

(52) U.S. Cl.
CPC ............ *A61F 2007/0039* (2013.01); *A61F 2007/0042* (2013.01); *A61F 2007/0056* (2013.01); *A61F 2007/0091* (2013.01); *A61F 2007/0093* (2013.01); *A61F 2007/0231* (2013.01); *A61H 2209/00* (2013.01)

(56) References Cited

U.S. PATENT DOCUMENTS

| | | |
|---|---|---|
| 2,504,308 A | 4/1950 | Donkle, Jr. |
| 3,014,117 A | 12/1961 | Madding |
| 3,164,152 A | 1/1965 | Vere Nicoll |
| 3,179,106 A * | 4/1965 | Meredith ............ A61H 9/0078 601/150 |
| 3,345,641 A | 10/1967 | Jennings |
| 3,367,319 A | 2/1968 | Carter, Jr. |
| 3,548,809 A | 12/1970 | Conti |
| 3,608,091 A | 9/1971 | Olson et al. |
| 3,660,849 A | 5/1972 | Jonnes et al. |
| 3,736,764 A | 6/1973 | Chambers et al. |
| 3,738,702 A | 6/1973 | Jacobs |
| 3,744,053 A | 7/1973 | Parker et al. |
| 3,744,555 A | 7/1973 | Fletcher et al. |
| 3,862,629 A | 1/1975 | Rotta |
| 3,894,213 A | 7/1975 | Agarwala |
| 4,006,604 A | 2/1977 | Seff |
| 4,013,069 A | 3/1977 | Hasty |
| 4,029,087 A | 6/1977 | Dye et al. |
| 4,206,751 A | 6/1980 | Schneider |
| 4,224,941 A | 9/1980 | Stivala |
| 4,375,217 A | 3/1983 | Arkans |
| 4,402,312 A | 9/1983 | Villari et al. |
| 4,419,988 A * | 12/1983 | Mummert ............ A61H 9/0078 601/150 |
| 4,459,468 A | 7/1984 | Bailey |
| 4,459,822 A | 7/1984 | Pasternack |
| 4,471,787 A | 9/1984 | Bentall |
| 4,503,484 A | 3/1985 | Moxon |
| 4,523,594 A * | 6/1985 | Kuznetz ............... A61F 7/02 607/104 |
| 4,547,906 A | 10/1985 | Nishida et al. |
| 4,590,925 A | 5/1986 | Dillon |
| 4,597,384 A | 7/1986 | Whitney |
| 4,608,041 A | 8/1986 | Nielsen |
| D285,821 S | 9/1986 | Kneisley |
| D288,372 S | 2/1987 | Adams |
| 4,660,388 A | 4/1987 | Greene, Jr. |
| 4,738,249 A | 4/1988 | Linman et al. |
| D295,897 S | 5/1988 | Thimm-Kelly |
| 4,741,338 A | 5/1988 | Miyamae |
| 4,795,435 A | 1/1989 | Steer |
| 4,821,354 A | 4/1989 | Little |
| 4,844,072 A | 7/1989 | French et al. |
| 4,884,304 A | 12/1989 | Elkins |
| 4,901,200 A | 2/1990 | Mazura |
| 4,911,231 A | 3/1990 | Horne et al. |
| 4,926,881 A | 5/1990 | Ichinomiya et al. |
| 4,962,761 A | 10/1990 | Golden |
| 4,979,375 A | 10/1990 | Nathans et al. |
| 4,969,881 A | 11/1990 | Viesturs |
| 4,989,589 A | 2/1991 | Pekanmaki et al. |
| 4,995,698 A | 2/1991 | Myers |
| 4,996,970 A | 3/1991 | Legare |
| 5,044,364 A | 9/1991 | Crowther |
| 5,051,562 A | 9/1991 | Bailey et al. |
| D320,872 S | 10/1991 | McCrane |
| 5,062,414 A | 11/1991 | Grim |
| 5,067,040 A | 11/1991 | Fallik |
| 5,080,089 A | 1/1992 | Mason et al. |
| 5,090,409 A | 2/1992 | Genis |
| 5,092,271 A | 3/1992 | Kleinsasser |
| 5,097,829 A | 3/1992 | Quisenberry |
| 5,106,373 A | 4/1992 | Augustine et al. |
| 5,112,045 A | 5/1992 | Mason et al. |
| 5,117,812 A | 6/1992 | McWhorter |
| 5,125,238 A | 6/1992 | Ragan et al. |
| 5,165,127 A | 11/1992 | Nicholson |
| 5,179,941 A | 1/1993 | Siemssen et al. |
| 5,184,612 A | 2/1993 | Augustine |
| 5,186,698 A | 2/1993 | Mason et al. |
| 5,230,335 A | 7/1993 | Johnson, Jr. et al. |
| 5,232,020 A | 8/1993 | Mason et al. |
| 5,241,951 A | 9/1993 | Mason et al. |
| 5,243,706 A | 9/1993 | Frim et al. |
| 5,261,399 A | 11/1993 | Klatz et al. |
| 5,263,538 A | 11/1993 | Amidieu et al. |
| 5,285,347 A | 2/1994 | Fox et al. |
| D345,082 S | 3/1994 | Wenzl |
| D345,609 S | 3/1994 | Mason et al. |
| D345,802 S | 4/1994 | Mason et al. |
| D345,803 S | 4/1994 | Mason et al. |
| 5,300,101 A | 4/1994 | Augustine et al. |
| 5,300,102 A | 4/1994 | Augustine et al. |
| 5,300,103 A | 4/1994 | Stempel et al. |
| 5,303,716 A | 4/1994 | Mason et al. |
| 5,315,994 A | 5/1994 | Guibert et al. |
| 5,316,250 A | 5/1994 | Mason et al. |
| D348,106 S | 6/1994 | Mason et al. |
| 5,323,847 A | 6/1994 | Koizumi et al. |
| 5,324,319 A | 6/1994 | Mason et al. |
| 5,324,320 A | 6/1994 | Augustine et al. |
| D348,518 S | 7/1994 | Mason et al. |
| 5,330,519 A | 7/1994 | Mason et al. |
| 5,336,250 A | 8/1994 | Augustine |
| 5,342,411 A | 8/1994 | Maxted et al. |
| 5,343,579 A | 9/1994 | Dickerhoff et al. |
| 5,350,417 A | 9/1994 | Augustine |
| D351,472 S | 10/1994 | Mason et al. |
| 5,352,174 A | 10/1994 | Mason et al. |
| 5,354,117 A | 10/1994 | Danielson et al. |
| D352,781 S | 11/1994 | Mason et al. |
| 5,360,439 A | 11/1994 | Dickerhoff et al. |
| 5,370,178 A | 12/1994 | Agonafer et al. |
| 5,371,665 A | 12/1994 | Quisenberry et al. |
| D354,138 S | 1/1995 | Kelly |
| D357,747 S | 4/1995 | Kelly |
| 5,402,542 A | 4/1995 | Viard |
| 5,405,370 A | 4/1995 | Irani |
| 5,405,371 A | 4/1995 | Augustine et al. |
| 5,407,421 A | 4/1995 | Goldsmith |
| D358,216 S | 5/1995 | Dye |
| 5,411,494 A | 5/1995 | Rodriguez |
| 5,411,541 A | 5/1995 | Bell et al. |
| 5,417,720 A | 5/1995 | Mason |
| 5,440,450 A | 8/1995 | Lau et al. |
| 5,449,379 A | 9/1995 | Hadtke |
| 5,466,250 A | 11/1995 | Johnson, Jr. et al. |
| 5,496,262 A | 3/1996 | Johnson, Jr. et al. |
| 5,496,357 A | 3/1996 | Jensen et al. |
| 5,505,726 A | 4/1996 | Meserol |
| 5,507,792 A | 4/1996 | Mason |
| 5,509,894 A | 4/1996 | Mason et al. |
| 5,514,079 A | 5/1996 | Dillon |
| 5,528,485 A | 6/1996 | Devilbiss et al. |
| 5,561,981 A | 10/1996 | Quisenberry et al. |
| 5,566,062 A | 10/1996 | Quisenberry et al. |
| D376,013 S | 11/1996 | Sandman et al. |
| 5,578,022 A | 11/1996 | Scherson et al. |
| 5,584,798 A * | 12/1996 | Fox ..................... A61H 9/0078 601/150 |
| 5,588,954 A | 12/1996 | Ribando et al. |
| 5,591,200 A | 1/1997 | Cone et al. |
| 5,603,728 A | 2/1997 | Pachys |
| 5,636,643 A | 6/1997 | Argenta et al. |

(56) References Cited

U.S. PATENT DOCUMENTS

| | | |
|---|---|---|
| D380,874 S | 7/1997 | Caswell |
| 5,645,081 A | 7/1997 | Argenta et al. |
| 5,648,716 A | 7/1997 | Devilbiss et al. |
| D383,546 S | 9/1997 | Amis et al. |
| D383,547 S | 9/1997 | Mason et al. |
| D383,848 S | 9/1997 | Mason et al. |
| 5,662,695 A | 9/1997 | Mason et al. |
| 5,669,872 A | 9/1997 | Fox |
| 5,672,152 A | 9/1997 | Mason et al. |
| 5,675,473 A | 10/1997 | McDunn et al. |
| 5,682,748 A | 11/1997 | DeVilbiss et al. |
| 5,689,957 A | 11/1997 | DeVilbiss et al. |
| 5,690,849 A | 11/1997 | DeVilbiss et al. |
| 5,711,029 A | 1/1998 | Visco et al. |
| 5,711,155 A | 1/1998 | DeVilbiss et al. |
| D393,073 S | 3/1998 | Downing et al. |
| 5,731,954 A | 3/1998 | Cheon |
| 5,733,321 A | 3/1998 | Brink |
| D394,707 S | 5/1998 | Tsubooka |
| 5,755,755 A | 5/1998 | Panyard |
| 5,772,618 A | 6/1998 | Mason et al. |
| 5,782,780 A | 7/1998 | Mason et al. |
| 5,795,312 A | 8/1998 | Dye |
| 5,807,294 A | 9/1998 | Cawley et al. |
| 5,827,208 A | 10/1998 | Mason |
| 5,831,824 A | 11/1998 | McDunn et al. |
| D403,779 S | 1/1999 | Davis et al. |
| D404,490 S | 1/1999 | Tripolsky |
| D405,884 S | 2/1999 | Roper |
| 5,865,841 A | 2/1999 | Kolen et al. |
| 5,871,526 A | 2/1999 | Gibbs et al. |
| 5,890,371 A | 4/1999 | Rajasubramanian et al. |
| 5,897,581 A | 4/1999 | Fronda et al. |
| 5,901,037 A | 5/1999 | Hamilton et al. |
| 5,913,885 A | 6/1999 | Klatz et al. |
| 5,923,533 A | 7/1999 | Olson |
| 5,947,914 A | 9/1999 | Augustine |
| 5,950,234 A | 9/1999 | Leong et al. |
| 5,980,561 A | 11/1999 | Kolen et al. |
| 5,989,285 A | 11/1999 | DeVilbiss et al. |
| 6,007,559 A | 12/1999 | Arkans |
| 6,030,412 A | 2/2000 | Klatz et al. |
| 6,055,157 A | 4/2000 | Bartilson |
| 6,058,010 A | 5/2000 | Schmidt et al. |
| 6,058,712 A | 5/2000 | Rajasubramanian et al. |
| 6,080,120 A | 6/2000 | Sandman et al. |
| D428,153 S | 7/2000 | Davis |
| D430,288 S | 8/2000 | Mason et al. |
| D430,289 S | 8/2000 | Mason et al. |
| 6,117,164 A | 9/2000 | Gildersleeve et al. |
| 6,125,036 A | 9/2000 | Kang et al. |
| 6,129,688 A | 10/2000 | Arkans |
| 6,135,116 A | 10/2000 | Vogel et al. |
| 6,156,059 A | 12/2000 | Olofsson |
| 6,176,869 B1 | 1/2001 | Mason et al. |
| 6,178,562 B1 | 1/2001 | Elkins |
| 6,186,977 B1 | 2/2001 | Andrews et al. |
| 6,231,532 B1 | 5/2001 | Watson et al. |
| 6,235,049 B1 | 5/2001 | Nazerian |
| 6,238,427 B1 | 5/2001 | Matta |
| 6,260,890 B1 | 7/2001 | Mason |
| 6,270,481 B1 | 8/2001 | Mason et al. |
| 6,277,143 B1 | 8/2001 | Klatz et al. |
| 6,295,819 B1 | 10/2001 | Mathiprakasam et al. |
| 6,305,180 B1 | 10/2001 | Miller et al. |
| 6,312,453 B1 | 11/2001 | Stefanile et al. |
| 6,319,114 B1 | 11/2001 | Nair et al. |
| 6,352,550 B1 | 3/2002 | Gildersleeve et al. |
| 6,358,219 B1 | 3/2002 | Arkans |
| 6,368,592 B1 | 4/2002 | Colton et al. |
| 6,436,064 B1 | 8/2002 | Kloecker |
| 6,443,978 B1 | 9/2002 | Zharov |
| 6,462,949 B1 | 10/2002 | Parish, IV et al. |
| 6,463,336 B1 | 10/2002 | Mawhinney |
| 6,468,237 B1 | 10/2002 | Lina |
| 6,508,831 B1 | 1/2003 | Kushnir |
| D472,322 S | 3/2003 | Hoglund et al. |
| D473,315 S | 4/2003 | Miros et al. |
| D473,656 S | 4/2003 | Miros et al. |
| D473,948 S | 4/2003 | Elkins et al. |
| 6,551,264 B1 | 4/2003 | Cawley et al. |
| 6,551,347 B1 * | 4/2003 | Elkins ............... A61F 7/0085 165/46 |
| D474,544 S | 5/2003 | Hoglund et al. |
| 6,562,060 B1 | 5/2003 | Momtaheni |
| 6,592,535 B2 | 7/2003 | Ravikumar |
| 6,596,016 B1 | 7/2003 | Vreman |
| 6,648,904 B2 | 11/2003 | Altshuler et al. |
| D484,601 S | 12/2003 | Griffiths et al. |
| D484,602 S | 12/2003 | Griffiths et al. |
| 6,660,027 B2 | 12/2003 | Gruszecki et al. |
| 6,667,883 B1 | 12/2003 | Solis et al. |
| 6,675,072 B1 | 1/2004 | Kerem |
| D486,870 S | 2/2004 | Mason |
| 6,695,823 B1 | 2/2004 | Lina et al. |
| 6,719,713 B2 | 4/2004 | Mason |
| 6,719,728 B2 | 4/2004 | Mason et al. |
| 6,736,787 B1 | 5/2004 | McEwen et al. |
| D492,411 S | 6/2004 | Bierman |
| 6,775,137 B2 | 8/2004 | Chu et al. |
| D496,108 S | 9/2004 | Machin et al. |
| 6,786,879 B1 * | 9/2004 | Bolam ............... A61H 9/0078 285/93 |
| 6,789,024 B1 | 9/2004 | Kochan, Jr. et al. |
| 6,802,823 B2 | 10/2004 | Mason |
| D499,846 S | 12/2004 | Cesko |
| 6,834,712 B2 | 12/2004 | Parish et al. |
| 6,846,295 B1 | 1/2005 | Ben-Nun |
| 6,848,498 B2 | 2/2005 | Seki et al. |
| 6,855,158 B2 | 2/2005 | Stolpmann |
| 6,893,414 B2 | 5/2005 | Goble et al. |
| D506,553 S | 6/2005 | Tesluk |
| 6,935,409 B1 | 8/2005 | Parish, IV et al. |
| 6,936,019 B2 | 8/2005 | Mason |
| D510,140 S | 9/2005 | Brown |
| 6,945,988 B1 | 9/2005 | Jones |
| D510,626 S | 10/2005 | Krahner et al. |
| 6,986,783 B2 | 1/2006 | Gunn et al. |
| D515,218 S | 2/2006 | McGuire et al. |
| 7,004,915 B2 | 2/2006 | Boynton et al. |
| D523,147 S | 6/2006 | Tesluk |
| 7,066,949 B2 | 6/2006 | Gammons et al. |
| 7,081,128 B2 | 7/2006 | Hart et al. |
| D533,668 S | 12/2006 | Brown |
| 7,195,624 B2 | 3/2007 | Lockwood et al. |
| 7,198,046 B1 | 4/2007 | Argenta et al. |
| 7,216,651 B2 | 5/2007 | Argenta et al. |
| D551,351 S | 9/2007 | Silva |
| D551,352 S | 9/2007 | Frangi |
| 7,306,568 B2 | 12/2007 | Diana |
| 7,354,411 B2 | 4/2008 | Perry et al. |
| D568,482 S | 5/2008 | Gramza et al. |
| D569,985 S | 5/2008 | Ganapathy et al. |
| 7,427,153 B1 | 9/2008 | Jacobs et al. |
| 7,429,252 B2 | 9/2008 | Sarangapani |
| 7,484,552 B2 | 2/2009 | Pfahnl |
| 7,492,252 B2 | 2/2009 | Maruyama |
| 7,524,286 B2 | 4/2009 | Johnson |
| 7,532,953 B2 | 5/2009 | Vogel |
| 7,553,306 B1 | 6/2009 | Hunt et al. |
| D595,620 S | 7/2009 | Kingsbury |
| D601,707 S | 10/2009 | Chouiller |
| 7,608,066 B2 | 10/2009 | Vogel |
| 7,618,382 B2 | 11/2009 | Vogel et al. |
| D608,006 S | 1/2010 | Avitable et al. |
| D612,947 S | 3/2010 | Turtzo et al. |
| D613,870 S | 4/2010 | Shust |
| 7,717,869 B2 | 5/2010 | Eischen, Sr. |
| D618,358 S | 6/2010 | Avitable et al. |
| D619,267 S | 7/2010 | Beckwith et al. |
| D620,122 S | 7/2010 | Cotton |
| 7,763,000 B2 | 7/2010 | Risk, Jr. et al. |
| 7,799,004 B2 | 9/2010 | Tumey |
| 7,804,686 B2 | 9/2010 | Parish et al. |

(56) References Cited

U.S. PATENT DOCUMENTS

| | | |
|---|---|---|
| D625,018 S | 10/2010 | Smith et al. |
| D626,241 S | 10/2010 | Sagnip et al. |
| D626,242 S | 10/2010 | Sagnip et al. |
| D626,243 S | 10/2010 | Sagnip et al. |
| D626,245 S | 10/2010 | Sagnip et al. |
| 7,811,269 B2 | 10/2010 | Boynton et al. |
| D627,896 S | 11/2010 | Matsuo et al. |
| D628,300 S | 11/2010 | Caden |
| 7,837,673 B2 | 11/2010 | Vogel |
| D630,759 S | 1/2011 | Matsuo et al. |
| 7,867,206 B2 | 1/2011 | Lockwood et al. |
| 7,871,387 B2 | 1/2011 | Tordella et al. |
| D631,971 S | 2/2011 | Turtzo et al. |
| D633,657 S | 3/2011 | Oban |
| D634,437 S | 3/2011 | Gramza et al. |
| D634,851 S | 3/2011 | Chiang |
| D635,266 S | 3/2011 | Chiang |
| D635,267 S | 3/2011 | Chiang |
| 7,896,864 B2 | 3/2011 | Lockwood et al. |
| 7,896,910 B2 | 3/2011 | Schirrmacher et al. |
| 7,909,861 B2 | 3/2011 | Balachandran et al. |
| D636,497 S | 4/2011 | Giaccone |
| D638,950 S | 5/2011 | Janzon |
| D640,380 S | 6/2011 | Tweardy et al. |
| D640,381 S | 6/2011 | Tweardy et al. |
| 7,959,588 B1 | 6/2011 | Wolpa |
| 8,007,491 B2 | 8/2011 | Pinto et al. |
| D649,648 S | 11/2011 | Cavalieri et al. |
| 8,052,630 B2 | 11/2011 | Kloecker et al. |
| 8,084,663 B2 | 12/2011 | Watson, Jr. |
| 8,088,113 B2 | 1/2012 | Scherson et al. |
| 8,100,956 B2 | 1/2012 | Quisenberry et al. |
| 8,109,981 B2 | 2/2012 | Gertner et al. |
| D655,420 S | 3/2012 | Bowles |
| D655,821 S | 3/2012 | Matsuo |
| 8,128,672 B2 | 3/2012 | Quisenberry et al. |
| 8,142,486 B2 | 3/2012 | Quisenberry et al. |
| D657,063 S | 4/2012 | Chiang |
| 8,157,792 B2 | 4/2012 | Dolliver et al. |
| D660,438 S | 5/2012 | Kennedy et al. |
| D660,439 S | 5/2012 | Chen et al. |
| D662,212 S | 6/2012 | Quisenberry |
| D662,213 S | 6/2012 | Quisenberry |
| D662,214 S | 6/2012 | Quisenberry |
| 8,202,262 B2 | 6/2012 | Lina et al. |
| D663,850 S | 7/2012 | Joseph |
| D664,260 S | 7/2012 | Quisenberry |
| D665,088 S | 8/2012 | Joseph |
| D665,470 S | 8/2012 | Galbraith |
| D666,258 S | 8/2012 | Campbell |
| D666,301 S | 8/2012 | Joseph |
| 8,240,885 B2 | 8/2012 | Miller |
| 8,248,798 B2 | 8/2012 | Parish et al. |
| D679,023 S | 3/2013 | Quisenberry |
| 8,425,580 B2 | 4/2013 | Quisenberry et al. |
| D683,042 S | 5/2013 | Quisenberry |
| 8,444,581 B1 | 5/2013 | Maxon-Maldonado et al. |
| 8,449,483 B2 | 5/2013 | Eddy |
| 8,485,995 B1 | 7/2013 | Maxon-Maldonado |
| 8,529,613 B2 | 9/2013 | Radziunas et al. |
| 8,569,566 B2 | 10/2013 | Blott et al. |
| 8,574,278 B2 | 11/2013 | Quisenberry |
| 8,632,576 B2 | 1/2014 | Quisenberry |
| 8,753,300 B2 | 6/2014 | Deshpande |
| 8,753,383 B2 | 6/2014 | Parish et al. |
| 8,758,419 B1 | 6/2014 | Quisenberry et al. |
| 8,772,567 B2 | 7/2014 | Eckstein et al. |
| 8,778,005 B2 | 7/2014 | Parish et al. |
| 8,827,935 B2 | 9/2014 | Maxon-Maldonado |
| 8,834,393 B2 | 9/2014 | Maxon-Maldonado et al. |
| 8,940,034 B2 | 1/2015 | Quisenberry |
| 9,101,463 B2 | 8/2015 | Stormby |
| 9,114,055 B2 | 8/2015 | Edelman et al. |
| 9,119,705 B2 * | 9/2015 | Parish ............ A61F 7/0085 |
| 9,132,057 B2 | 9/2015 | Wilford et al. |
| 9,180,041 B2 | 11/2015 | Parish et al. |
| 9,192,539 B2 | 11/2015 | Parish et al. |
| 9,669,233 B2 | 6/2017 | Quisenberry et al. |
| 2001/0018604 A1 | 8/2001 | Elkins |
| 2001/0039439 A1 | 11/2001 | Elkins et al. |
| 2002/0058976 A1 | 5/2002 | Lee |
| 2002/0116041 A1 | 8/2002 | Daoud |
| 2002/0143373 A1 | 10/2002 | Courtnage et al. |
| 2003/0050594 A1 | 3/2003 | Zamierowski |
| 2003/0054046 A1 | 3/2003 | Burrell et al. |
| 2003/0083610 A1 | 5/2003 | McGrath et al. |
| 2003/0089486 A1 | 5/2003 | Parish et al. |
| 2003/0089487 A1 | 5/2003 | Parish, IV et al. |
| 2003/0125649 A1 * | 7/2003 | McIntosh ............ A61H 9/0071 601/15 |
| 2003/0127215 A1 | 7/2003 | Parish, IV et al. |
| 2003/0135252 A1 | 7/2003 | MacHold et al. |
| 2003/0139255 A1 * | 7/2003 | Lina ............ A61F 13/065 482/24 |
| 2003/0163183 A1 | 8/2003 | Carson |
| 2003/0171703 A1 | 9/2003 | Grim et al. |
| 2003/0176822 A1 | 9/2003 | Morgenlander |
| 2003/0191437 A1 | 10/2003 | Knighton et al. |
| 2004/0008483 A1 | 1/2004 | Cheon |
| 2004/0030281 A1 | 2/2004 | Goble et al. |
| 2004/0046108 A1 | 3/2004 | Spector |
| 2004/0054307 A1 | 3/2004 | Mason et al. |
| 2004/0068309 A1 | 4/2004 | Edelman |
| 2004/0068310 A1 | 4/2004 | Edelman |
| 2004/0099407 A1 | 5/2004 | Parish, IV et al. |
| 2004/0133135 A1 | 7/2004 | Diana |
| 2004/0176805 A1 | 9/2004 | Whelan et al. |
| 2004/0186535 A1 | 9/2004 | Knowlton |
| 2004/0193218 A1 | 9/2004 | Butler |
| 2004/0210176 A1 | 10/2004 | Diana |
| 2004/0221604 A1 | 11/2004 | Ota et al. |
| 2004/0260231 A1 | 12/2004 | Goble et al. |
| 2005/0004636 A1 | 1/2005 | Noda et al. |
| 2005/0006061 A1 | 1/2005 | Quisenberry et al. |
| 2005/0033390 A1 | 2/2005 | McConnell |
| 2005/0039887 A1 | 2/2005 | Parish, IV et al. |
| 2005/0070828 A1 | 3/2005 | Hampson et al. |
| 2005/0070835 A1 | 3/2005 | Joshi |
| 2005/0080465 A1 | 4/2005 | Zelickson et al. |
| 2005/0126578 A1 * | 6/2005 | Garrison ............ A61H 9/0078 128/874 |
| 2005/0133214 A1 | 6/2005 | Pfahnl |
| 2005/0143797 A1 | 6/2005 | Parish et al. |
| 2005/0177093 A1 | 8/2005 | Barry et al. |
| 2005/0182364 A1 | 8/2005 | Burchman |
| 2005/0187500 A1 | 8/2005 | Perry et al. |
| 2005/0256556 A1 | 11/2005 | Schirrmacher et al. |
| 2005/0274120 A1 | 12/2005 | Quisenberry et al. |
| 2005/0284615 A1 | 12/2005 | Parish et al. |
| 2006/0034053 A1 | 2/2006 | Parish et al. |
| 2006/0035122 A1 | 2/2006 | Weissman et al. |
| 2006/0058714 A1 | 3/2006 | Rhoades |
| 2006/0116620 A1 | 6/2006 | Oyaski |
| 2006/0167531 A1 | 7/2006 | Gertner et al. |
| 2006/0217787 A1 | 9/2006 | Olson et al. |
| 2006/0241549 A1 | 10/2006 | Sunnen |
| 2006/0253089 A1 | 11/2006 | Lin |
| 2006/0276845 A1 | 12/2006 | George et al. |
| 2006/0282028 A1 | 12/2006 | Howard et al. |
| 2007/0032778 A1 | 2/2007 | Heaton et al. |
| 2007/0068651 A1 | 3/2007 | Gammons et al. |
| 2007/0112401 A1 | 5/2007 | Balachandran et al. |
| 2007/0118194 A1 | 5/2007 | Mason et al. |
| 2007/0129658 A1 | 6/2007 | Hampson et al. |
| 2007/0233209 A1 | 10/2007 | Whitehurst |
| 2007/0239232 A1 | 10/2007 | Kurtz et al. |
| 2007/0260162 A1 | 11/2007 | Meyer et al. |
| 2007/0282249 A1 | 12/2007 | Quisenberry |
| 2008/0058911 A1 | 3/2008 | Parish et al. |
| 2008/0064992 A1 | 3/2008 | Stewart et al. |
| 2008/0071330 A1 | 3/2008 | Quisenberry |
| 2008/0082029 A1 | 4/2008 | Diana |
| 2008/0103397 A1 | 5/2008 | Barak |
| 2008/0103422 A1 | 5/2008 | Perry et al. |

(56) References Cited

U.S. PATENT DOCUMENTS

| | | |
|---|---|---|
| 2008/0125775 A1 | 5/2008 | Morris |
| 2008/0132816 A1 | 6/2008 | Kane et al. |
| 2008/0132976 A1 | 6/2008 | Kane et al. |
| 2008/0249559 A1 | 10/2008 | Brown et al. |
| 2008/0262399 A1 | 10/2008 | Kovelman et al. |
| 2008/0319362 A1 | 12/2008 | Joseph |
| 2009/0069731 A1 | 3/2009 | Parish et al. |
| 2009/0076475 A1 | 3/2009 | Ross et al. |
| 2009/0109622 A1 | 4/2009 | Parish et al. |
| 2009/0149821 A1 | 6/2009 | Scherson et al. |
| 2009/0237264 A1 | 9/2009 | Bobey |
| 2009/0254159 A1 | 10/2009 | Stormby |
| 2009/0254160 A1 | 10/2009 | Shawver et al. |
| 2010/0010477 A1 | 1/2010 | Augustine et al. |
| 2010/0030306 A1 | 2/2010 | Edelman et al. |
| 2010/0081975 A1 | 4/2010 | Avitable et al. |
| 2010/0121230 A1 | 5/2010 | Vogel et al. |
| 2010/0137764 A1 | 6/2010 | Eddy |
| 2010/0145421 A1 | 6/2010 | Tomlinson et al. |
| 2010/0150991 A1 | 6/2010 | Bernstein |
| 2010/0160838 A1 | 6/2010 | Krespi |
| 2010/0179469 A1 | 7/2010 | Hammond et al. |
| 2010/0186436 A1 | 7/2010 | Stormby |
| 2010/0210982 A1 | 8/2010 | Balachandran et al. |
| 2010/0249679 A1 | 9/2010 | Perry et al. |
| 2010/0249680 A1 | 9/2010 | Davis |
| 2010/0305524 A1 | 12/2010 | Vess et al. |
| 2010/0331797 A1 | 12/2010 | Patel et al. |
| 2011/0009785 A1 | 1/2011 | Meyer et al. |
| 2011/0034861 A1 | 2/2011 | Schaefer |
| 2011/0037002 A1 | 2/2011 | Johnson et al. |
| 2011/0071447 A1 | 3/2011 | Liu et al. |
| 2011/0082401 A1 | 4/2011 | Iker et al. |
| 2011/0087142 A1 | 4/2011 | Ravikumar et al. |
| 2011/0245788 A1 | 10/2011 | Marquez Canada |
| 2011/0275983 A1 | 11/2011 | Quisenberry et al. |
| 2011/0282269 A1 | 11/2011 | Quisenberry et al. |
| 2012/0041526 A1 | 2/2012 | Stormby |
| 2012/0130457 A1 | 5/2012 | Gammons et al. |
| 2012/0259266 A1 | 10/2012 | Quisenberry |
| 2012/0289885 A1 | 11/2012 | Cottrell et al. |
| 2013/0030331 A1 | 1/2013 | Quisenberry et al. |
| 2013/0030395 A1 | 1/2013 | Croizat et al. |
| 2013/0103123 A1 | 4/2013 | Khan et al. |
| 2013/0116612 A1 | 5/2013 | Stephan |
| 2013/0191437 A1 | 7/2013 | Itoh |
| 2013/0216627 A1 | 8/2013 | Galbraith et al. |
| 2013/0245508 A1 | 9/2013 | Maxon-Maldonado |
| 2013/0245519 A1 | 9/2013 | Edelman et al. |
| 2013/0253383 A1 | 9/2013 | Maxon-Maldonado |
| 2013/0261512 A1 | 10/2013 | Maxon-Maldonado et al. |
| 2013/0281947 A1 | 10/2013 | Quisenberry |
| 2013/0331767 A1 | 12/2013 | Quisenberry |
| 2014/0012169 A1 | 1/2014 | Wilford et al. |
| 2014/0046410 A1 | 2/2014 | Wyatt |
| 2014/0052054 A1 | 2/2014 | Quisenberry |
| 2014/0236271 A1 | 8/2014 | Fronda et al. |
| 2014/0257175 A1 | 9/2014 | Quisenberry |
| 2014/0316330 A1 | 10/2014 | Fudem et al. |
| 2014/0323949 A1 | 10/2014 | Quisenberry |
| 2015/0133849 A1 | 5/2015 | Quisenberry et al. |
| 2015/0290364 A1 | 10/2015 | Wall et al. |
| 2015/0328042 A1 | 11/2015 | Parish et al. |
| 2016/0030236 A1 | 2/2016 | Parish et al. |
| 2016/0067104 A1 | 3/2016 | Sarangapani et al. |
| 2016/0082238 A1 | 3/2016 | Wells et al. |
| 2016/0317348 A1 | 11/2016 | Banker |
| 2017/0119940 A1 | 5/2017 | Quisenberry |
| 2018/0369462 A1 | 12/2018 | Anderson et al. |

FOREIGN PATENT DOCUMENTS

| | | |
|---|---|---|
| EP | 0076074 A1 | 4/1983 |
| EP | 0 489 326 | 6/1992 |
| EP | 0864309 A2 | 9/1998 |
| GB | 2373444 A | 9/2002 |
| JP | 2009504246 A | 2/2009 |
| SU | 689674 | 10/1979 |
| WO | WO-82/04184 A1 | 12/1982 |
| WO | WO-1989009583 A2 | 10/1989 |
| WO | WO-93/09727 | 5/1993 |
| WO | WO-93/12708 A2 | 7/1993 |
| WO | WO-1996005873 A1 | 2/1996 |
| WO | WO-9807397 A1 | 2/1998 |
| WO | WO-1998016176 A1 | 4/1998 |
| WO | WO-00/40186 | 7/2000 |
| WO | WO-01/14012 A1 | 3/2001 |
| WO | WO-01/54635 A1 | 8/2001 |
| WO | WO-03/047479 A1 | 6/2003 |
| WO | WO-2004103452 A1 | 12/2004 |
| WO | WO-2004105676 A1 | 12/2004 |
| WO | WO-2005046760 A1 | 5/2005 |
| WO | WO-2007019038 A2 | 2/2007 |
| WO | WO-2008099017 A1 | 8/2008 |
| WO | WO-2010124234 A1 | 10/2010 |
| WO | WO-2012067918 A1 | 5/2012 |

OTHER PUBLICATIONS

U.S. Appl. No. 15/370,689, Quisenberry.
U.S. Appl. No. 12/730,060, Parish et al.
U.S. Appl. No. 12/708,422, Balachandran et al.
U.S. Appl. No. 12/871,188, Parish et al.
U.S. Appl. No. 13/107,264, Quisenberry.
U.S. Appl. No. 12/364,434, Quisenberry.
U.S. Appl. No. 13/190,564, Quisenberry et al.
U.S. Appl. No. 29,397,856, Quisenberry.
U.S. Appl. No. 29/400,194, Quisenberry.
U.S. Appl. No. 29/400,202, Quisenberry.
U.S. Appl. No. 29/400,212, Quisenberry.
U.S. Appl. No. 29/402,115, Quisenberry.
U.S. Appl. No. 13/796,139, Quisenberry.
U.S. Appl. No. 13/962,994, Quisenberry.
U.S. Appl. No. 14/062,428, Quisenberry.
U.S. Appl. No. 14/197,324, Quisenberry.
Artikis, T., PCT International Preliminary Report on Patentability dated Jul. 29, 2005, (10 pgs.).
Tom Lee, T.Y. et al; "Compact Liquid Cooling System for Small, Moveable Electronic Equipment", IEEE Transactions on Components, Hybrids, and Manufacturing Technology, Oct. 15, 1992, vol. 15, No. 5, pp. 786-793.
Copenheaver, Blaine R., "International Search Report" for PCT/US2007/022148 dated Apr. 2, 2008, 2 pages.
Young, Lee W., "International Search Report" for PCT/US07/08807 dated Mar. 3, 2008, (3 pages).
Mahmoud Karimi Azar Daryany, et al., "Photoinactivation of *Escherichia coli* and *Saccharomyces cerevisiae* Suspended in Phosphate-Buffered Saline-A Using 266- and 355-nm Pulsed Ultraviolet Light", Curr Microbiol, vol. 56, 2008, pp. 423-428.
J. Li, et al., "Enhanced germicidal effects of pulsed UV-LED irradiation on biofilms", Journal of . Applied Microbiology, 2010, pp. 1-8.
Cyro/Temp Therapy Systems; Product News Catalogue; Jobst Institute, Inc., 6 pages (Copyright 1982).
Quisenberry, Tony, "U.S. Appl. No. 13/359,210", filed Jan. 26, 2012.
Quisenberry, Tony, "U.S. Appl. No. 29/424,860", filed Jun. 15, 2012.
Quisenberry, Tony, "U.S. Appl. No. 13/456,410", filed Apr. 26, 2012.
Copenheaver, Blaine R., "International Search Report" for PCT/US2012/035096 dated Aug. 7, 2012, 3 pages.
Quisenberry, Tony, "U.S. Appl. No. 13/558,615", filed Jul. 26, 2012.
Copenheaver, Blaine R., "International Search Report" prepared for PCT/US2013/030475 dated May 23, 2013, 3 pages.
Young, Lee W., International Search Report of PCT Application No. PCT/US2014/64805, dated Mar. 13, 2015 (3 pages).

(56) References Cited

OTHER PUBLICATIONS

Hair Science Systems LLC, "Hair Science Systems—01 mobile unit—", Hair Saver Chemo Cold Cap, www.hairsciencesystems.com, 2 pages.

"U.S. FDA de novo clearance for the DigniCap® scalp cooling system that reduces hair loss related to chemotherapy for women with breast cancer", www.sysmex-europe.com/company/news-and -events/press-releases, accessed on Jun. 17, 2016, 3 pages.

"DigniLife—Prevention of Chermotherapy-Induced Alopecia", www.sysmex.co.uk/products/oncology/scalp-cooling-system-dignilife, accessed on Jun. 17, 2016, 3 pages.

\* cited by examiner

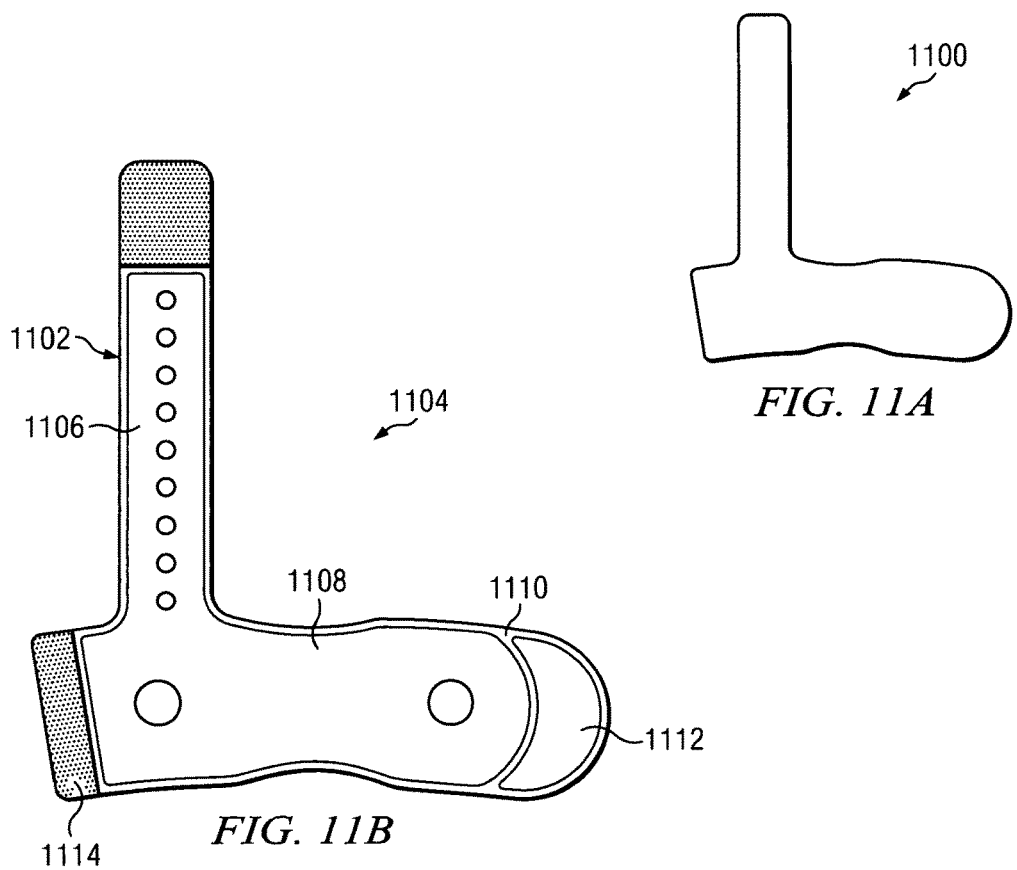
FIG. 11A
FIG. 11B
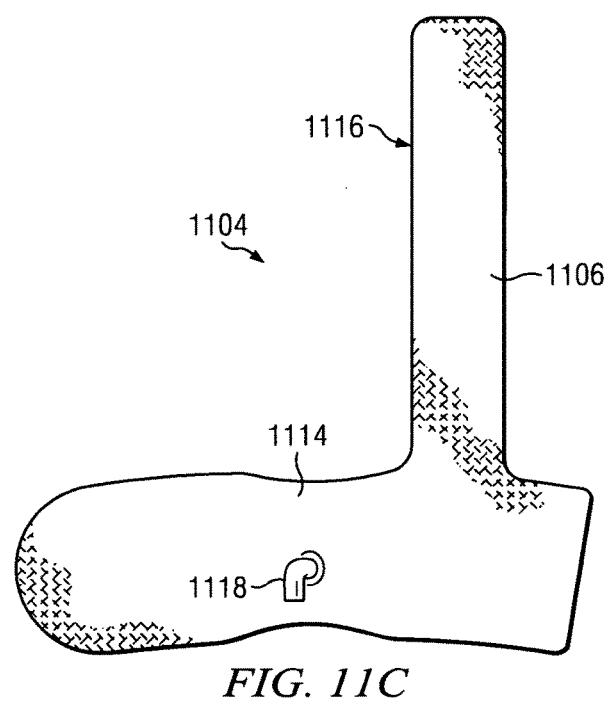
FIG. 11C

METHOD AND SYSTEM FOR THERMAL AND COMPRESSION THERAPY RELATIVE TO THE PREVENTION OF DEEP VEIN THROMBOSIS

CROSS-REFERENCE TO RELATED APPLICATIONS

The present application is a continuation of U.S. patent application Ser. No. 11/733,709, filed Apr. 10, 2007, now U.S. Pat. No. 9,119,705. U.S. patent application Ser. No. 11/733,709 claims priority from, and incorporates by reference for any purpose the entire disclosure of each of U.S. Provisional Patent Application Ser. No. 60/791,132 filed Apr. 11, 2006 and U.S. Provisional Patent Application Ser. No. 60/817,932 filed Jun. 30, 2006. This application hereby incorporates by reference commonly assigned U.S. Pat. Nos. 5,097,829, 5,989,285, and U.S. Patent Application Serial Nos. 60/488,709 filed Jul. 18, 2003, 60/550,658 filed Mar. 5, 2004, 60/558,453 filed Jul. 16, 2004, Ser. No. 09/328,183 filed Jun. 8, 1998, and Ser. No. 10/894,369 filed Jul. 19, 2004. U.S. patent application Ser. No. 11/733,709 and U.S. Provisional Patent Application Nos. 60/791,132 and 60/817,932 are each incorporated herein by reference.

BACKGROUND OF THE INVENTION

Technical Field

The present invention relates to medical therapy systems in general, including therapeutic cooling, heating, and compression systems used in association therewith, and more particularly, but not by way of limitation, to a programmable, thermal therapy and external pneumatic compression for the prevention of deep vein thrombosis.

Description of the Related Art

Considerable medical attention has been given to the serious medical issue of Deep Vein Thrombosis ("DVT"). One approach to the prevention of DVT has been External Pneumatic Compressions ("EPC"). EPC has been shown to be helpful as a prophylaxis for DVT, although refinements over existing systems are still in need. For example, multiple articles have been written addressing this issue, including a compilation of recommendations for preventing DVT (Heit J A: Current Recommendations for Prevention of Deep Venous Thrombosis. In: *Handbook of Venous Disorders*. Gloviczki P, Yao J S, eds. Cambridge, The University Press, 1996). Engineering studies are presented which also address EPC as a preventative for DVT (Kamm R D: Bioengineering Studies of Periodic External Compression as Prophylaxis Against Deep Vein Thrombosis—Part 1: Numerical Studies. *J Biomech Engineering* 104(1): 87-95, 1982). Such efforts are meritorious for patient health due to possible Pulmonary Embolism ("PE") resulting from DVT (National Institutes of Health Consensus Development Conference Statement: Prevention of Venous Thrombosis and Pulmonary Embolism. *JAMA* 6(2) 744-749, 1986). Additionally, studies have been performed relative to DVT and orthopedic surgery ("OS") (Westrich G H, Sculco T P: Prophylaxis Against Deep Vein Thrombosis After Total Knee Arthroplasty. *J Bone Joint Surg* 78-A(6): 826-834, 1996).

Relative to OS, physicians have long recognized the need to provide warmth and cooling directly to patients as part of OS therapy. Better recoveries have been reported, for example, using cold therapy for orthopedic patients. The benefits of warming patients undergoing surgery has also been demonstrated. It may also be desirable to cool portions of a patient's anatomy in certain circumstances. Yet another advantageous therapy is the application of heat then cold to certain injured areas. See, for example, U.S. Pat. No. 5,989,285 (the '285 patent) assigned to Thermotek, Inc. and incorporated herein by reference.

Several devices have been developed that deliver temperature-controlled fluids through pads or convective thermal blankets to achieve the above thermal purpose. Typically these devices have a heating or a cooling element, a source for the fluid, a pump for forcing the fluid through the pad or blanket, and a thermal interface between the patient and the temperature-controlled fluid. U.S. Pat. No. 4,884,304 to Elkins is directed to a mattress-cover device that contains liquid flow channels that provide the selective heating or cooling by conduction.

Devices have also been developed for providing heat to a person in bed. Electric blankets containing electric heating elements have been used for years to warm a person in bed. Cooling blankets, such as the blanket disclosed in U.S. Pat. No. 4,660,388 to Greene, have also been proposed. Greene discloses a cooling cover having an inflatable pad with plenum chambers at opposite ends thereof. Cool air is generated in a separate unit and directed to the pad and out a number of apertures on the underside of the pad and against the body of the person using the cover.

A disposable heating or cooling blanket that has three layers of flexible sheeting is disclosed in U.S. Pat. No. 5,125,238 to Ragan, et al. Two of the layers form an air chamber and the third includes a comfortable layer for contact with the patient. Conditioned air is directed toward the covered person through a multiplicity of orifices in the bottom layers of the blanket.

The temperature-controlled blanket and bedding assembly disclosed in the '285 patent includes a temperature-controlled blanket and temperature-controlled bedding system that provide both recirculating temperature-controlled fluid and temperature-controlled gas to enhance performance for convectively heating or cooling a patient. Counter-flow or co-flow heat-exchanging principles between the temperature-controlled liquid and the temperature-controlled gas achieve temperature uniformity across different sections of the blanket and the bedding system. Drapes and the temperature-controlled bedding system provide a temperature-controlled envelope around a person using the bedding system. In one embodiment of the bedding system, an air portion of the bedding system is provided that supplies a fluid portion of the overall bedding system. In another embodiment of the bedding system, the fluid portion of the bedding system is provided for use with a patient bed that supplies the air portion of the overall bedding system.

U.S. Pat. No. 5,097,829 to Quisenberry describes an improved temperature-controlled fluid-circulating system for automatically cooling a temperature-controlled fluid in a thermal blanket with a thermoelectric-cooling device having a cold side and a hot side when powered by electricity. The temperature-controlled fluid is cooled by a cold side of the cooling device and is pumped through, to, and from the blanket through first and second conduits.

BRIEF SUMMARY OF THE INVENTION

The present invention relates to thermal therapy and DVT compression system for use in heating or cooling a patient. In one aspect of the invention, a DVT therapy system includes at least a control unit adapted, a thermal-treatment blanket, a compressive-therapy treatment device, a first set of connector tubes, and a second set of connector tubes. The control unit is adapted to heat and cool a heat-transfer liquid within about 37-105° F. and to provide compressed air at a pressure of at least 25 mmHg above ambient atmospheric pressure. The thermal-treatment blanket is adapted for receipt of the transfer liquid from the control unit and to send the heat-transfer liquid back to the control unit, a compressive-therapy treatment device adapted to utilize the compressed air from the control unit, and a first and second set of connector tubes. The first set of connector tubes is adapted to facilitate the flow of the heat-transfer liquid between the control unit and the thermal treatment blanket. The second set of connector tubes is adapted to facilitate the flow of the compressed air between the control unit and the compressive treatment device.

In another aspect, a DVT method includes providing a control unit adapted to heat and cool a heat-transfer liquid to a temperature within the range of about 37-105° F. and adapted to provide compressed air at a pressure of at least 25 mmHg above ambient atmospheric pressure, providing a thermal treatment blanket adapted for receipt of the heat-transfer liquid from the control unit and for sending the heat-transfer liquid back to the control unit, and applying a hot or cold treatment to an individual's skin area. The method also includes providing a compressive-therapy treatment device utilizing the compressed air from the control unit and applying a compressive treatment to an individual's skin area. The method further includes providing a first set of connector tubes adapted to connect the control unit and the thermal treatment blanket to facilitate the flow of the heat-transfer liquid therebetween, and providing a second set of connector tubes adapted to connect the control unit and the compressive treatment device to facilitate the flow of the compressed air therebetween.

In a further aspect of the invention, a DVT therapy treatment device includes an upper and lower sheet of biocompatible material, a first air-tight, inflatable portion, a second air-tight inflatable portion, a first hook-and-loop fastener, a second-hook-and-loop fastener, and an inlet. The upper and lower sheet sheets have substantially the same shape and are sealed on an outer edge thereof. The first air-tight inflatable portion includes an elongated strap formed from both the upper and lower sheets, with the elongated strap being adapted to wrap around an individual's ankle. The second air-tight inflatable portion is attached to the first portion, has two longer sides that are relatively pinched at a location generally in the middle of the longer sides and two shorter sides, and is formed from the upper and lower sheets. The first hook-and-loop fastener is on a distal end on the first portion at a location away from the second portion. The second hook-and-loop fastener is disposed on a left edge of the second portion and is adapted to mate with the first hook-and-loop fastener to secure the DVT therapy device to the individual's foot for subsequent compressive therapy.

In yet another aspect of the invention, a DVT therapy device includes a first and second sheet of biocompatible material of a generally trapezoidal shape having concentric arcuate top and bottom edges, the first and second sheet being sealed on an outer edge thereof to create an air-tight inflatable structure, a first and second weld located symmetrically about the center of the first and second sheet, a third and fourth weld extending from the first and second welds respectively to create an 'S' shaped portion disposed in the center of the first and second welds, and an inlet for receipt of compressed air from the control unit, the inlet allowing the compressed air to inflate the 'S' shaped portion to facilitate compressive treatment of the individual's calf.

BRIEF DESCRIPTION OF THE DRAWINGS

A more complete understanding of the method and apparatus of the present invention may be obtained by reference to the following Detailed Description when taken in conjunction with the accompanying Drawings wherein:

FIGS. 11A-11G illustrate a DVT foot wrap;

DETAILED DESCRIPTION OF ILLUSTRATIVE EMBODIMENTS OF THE INVENTION

Applicants have discovered that the use of both thermal therapy and compression therapy during and for post-surgical treatment for the prevention of DVT is advantageous. As referenced above, numerous articles have been written on the problems associated with DVT and the utilization of thermal therapy is already well known. Consistent therewith, methods of and apparatuses for providing pressurized and thermally controlled fluids for use with patients in need of such therapy are disclosed. A versatile control unit is adapted for providing one of a plurality of treatment modalities. As described below, in one modality, a thermally controlled liquid is produced and provided in a configuration facilitating flow through a treatment pad or blanket for thermal therapy. In a second embodiment, air compression is provided such that a blanket can receive a flow of pressurized air to cause a degree of compression relative to the patient. In a third embodiment, DVT system modules are provided so that the prevention of DVT can be afforded. In a fourth embodiment, thermal therapy is provided with DVT treatment.

As further described below, a control unit will be shown to be provided with (a) thermally controlled fluid, (b) thermally controlled fluid and compression air, and (c) thermally controlled fluid, compression air, and DVT systems. The control unit for providing these selective features is described within a single chassis design capable of providing any of the modalities therein or herein described. This selective versatility provides financial and manufacturing incentives in that the simple design selectively can provide an industrial, medical, or electro-optic version that produces only thermally controlled liquid, such as co-liquid for cooling industrial equipment, in a configuration adaptable for other applications. Therefore, in one embodiment of the invention, the production of a control unit adapted only for chilling electronic components is conceivable while the same chassis and initial components place therein may also be adaptable for a version that provides a prophylaxis for DVT.

Figure 1:
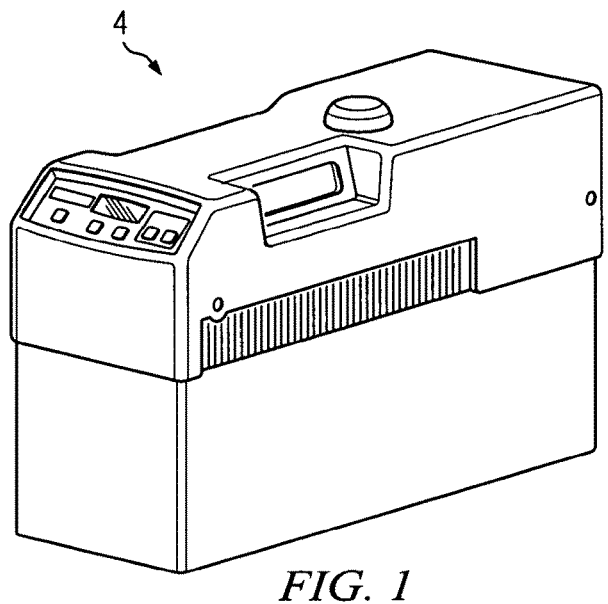
FIG. 1 is a perspective view of a thermal and compression-control system for thermal and compression therapy relative to the prevention of DVT.

Referring first to FIG. 1, there is shown a thermal and compression-control unit 4 for thermal and compression therapy. The control unit 4 is coupled to thermal and compression elements applied to a patient as described below. In this particular view, the control unit 4 is shown in perspective to illustrate the assembly of one embodiment of a control unit for pumping air and liquid through tubes to be described below for a patient to be treated therewith.

Referring still to FIG. 1, a lower dark portion thereof includes a filter that is removable from around a grate as illustrated below. In one embodiment, the filter provides an air-filtering substance such as woven netting that is attached by VELCRO fasteners or the like outwardly of a perforated metal grate to allow for the low pressure drawing of air therethrough to allow cooling of components placed inwardly therein prior to the upward draw of the air through fans disposed thereabove and the forcing of said air upwardly across a heat transfer assembly (HTA) 202 as presented in FIG. 2.

Figure 2:
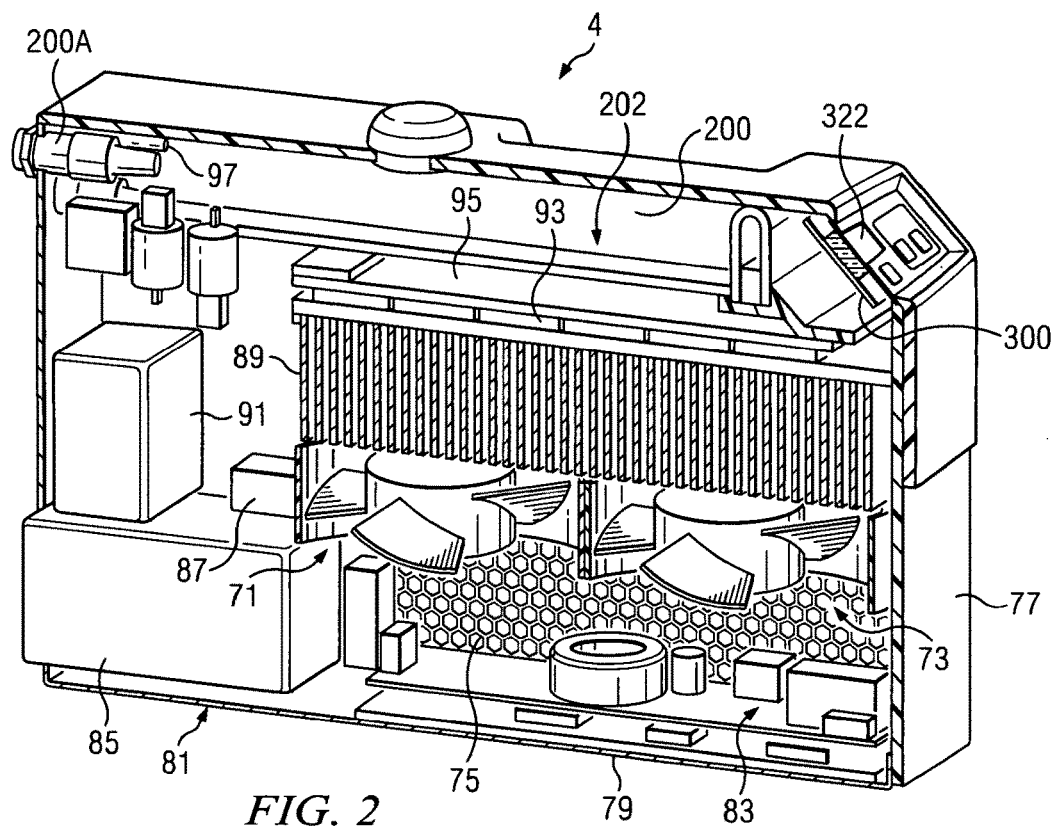
FIG. 2 is a cut-away, perspective view of the system of FIG. 1 illustrating various elements thereof.

Referring now to FIG. 2 specifically, the HTA 202 is shown disposed beneath a fluid reservoir 200. The reservoir 200 is adapted for storage of liquid that may be pumped outwardly through a fluid connector disposed rearwardly of the reservoir 200. Fluid connector 200A is adapted for connecting to the patient pads or blankets as described below.

Still referring to FIG. 2, there is shown the internal portion of the control unit 4 referenced above illustrating one embodiment of the assembly therein. Within the assembly of the unit 4, a pair of fans 71 and 73 are shown disposed above a grate 75. Grate 75 contains therearound the filter portion 77 that may be secured thereto by hook and loop (e.g., VELCRO). The lower portion of the grate is connected to a bottom portion 79 of a chassis 81 in a manner to provide support for electronic components 83 mounted thereon for providing the adequate power supply to and control of the HTA 202 and other elements within the control unit 4.

Referring specifically now to a dual-fan arrangement, fans are positioned to suck air from around the filtered grated region disposed peripherally about the electronic components so that the air flow is both quiet and at a rate allowing initial electronic cooling and then being available to be pushed into the top section of the control unit 4 where most heat dissipation is needed. In essence, the control unit 4 facilitates pulling air through the lower power supply that could then be forced upwardly for maximum cooling where maximum thermal change is needed.

Referring still to FIG. 2, an air pump 85 is disposed in a lower portion of a chassis 81 and beneath an air switch 87 disposed beneath a heat sink 89 disposed adjacent to a fluid pump 91. The fluid pump 91 is disposed in position for collecting fluid from a reservoir 200 that has been thermally controlled by the HTA 202 for passage through the fluid connector 200A. Thermal electric chips (TEC chips) 93 are shown disposed between the heat sink 89 and a thermal transfer plate 95 in a manner to provide the requisite thermal control of the fluid within the reservoir 200. An air connector 97 is shown disposed adjacent to the fluid connector 200A to provide the requisite dissipation of air from the air pump 85 for use in conjunction with the blanket 8 for application of pressure in a bladder forcing the thermal fluid flowing from the fluid connector 200A to be in close contact with the patient as described below.

Figure 3:
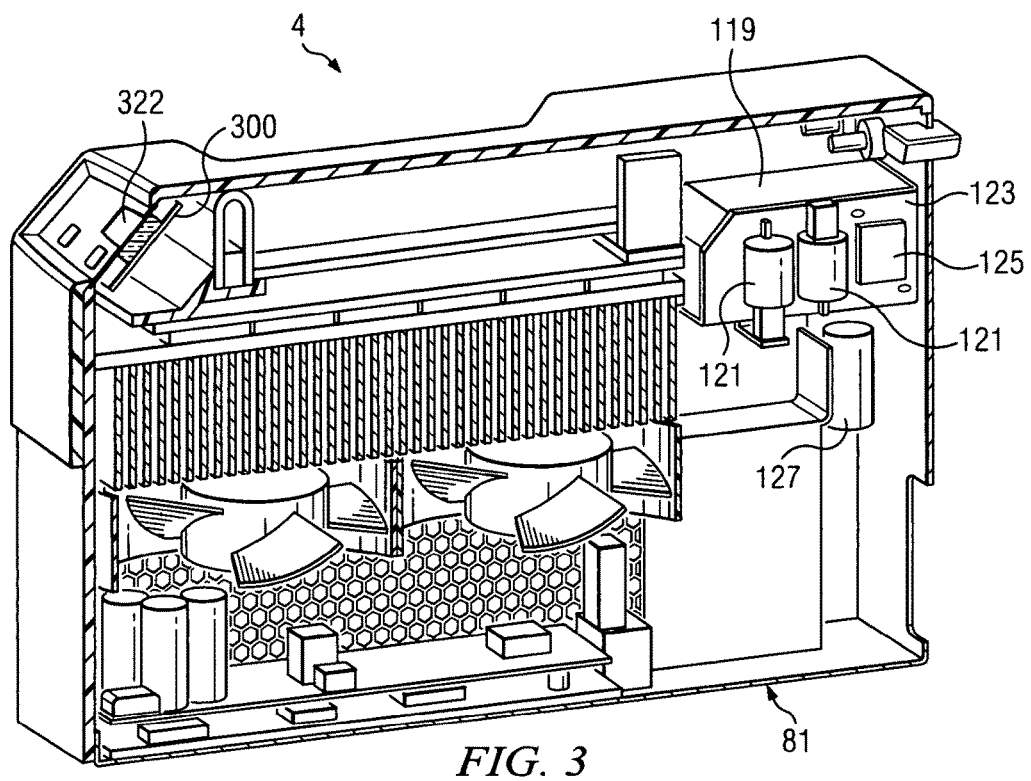
FIG. 3 is a cut-away, perspective view of the system of FIG. 1 taken from the opposite side of that in FIG. 2.

Referring now to FIG. 3, there is shown a cutaway perspective view of the control unit 4 taken from the opposite side thereof and illustrating various other aspects therein. Relative to this particular view of the control unit 4, a 500-watt power supply is shown disposed along with a 65-watt power supply relative to the chassis 81. The various power supplies are further defined herein and provide the requisite performance necessary for both flexibility and reliability. In conjunction with the DVT therapy operation, a DVT air pump 119 is shown disposed adjacent to a pair of DVT solenoids 121 mounted on a DVT air bracket 123 adjacent a DVT air switch 125. A pair of solenoids 127 are likewise disposed relative thereto.

Figure 4:
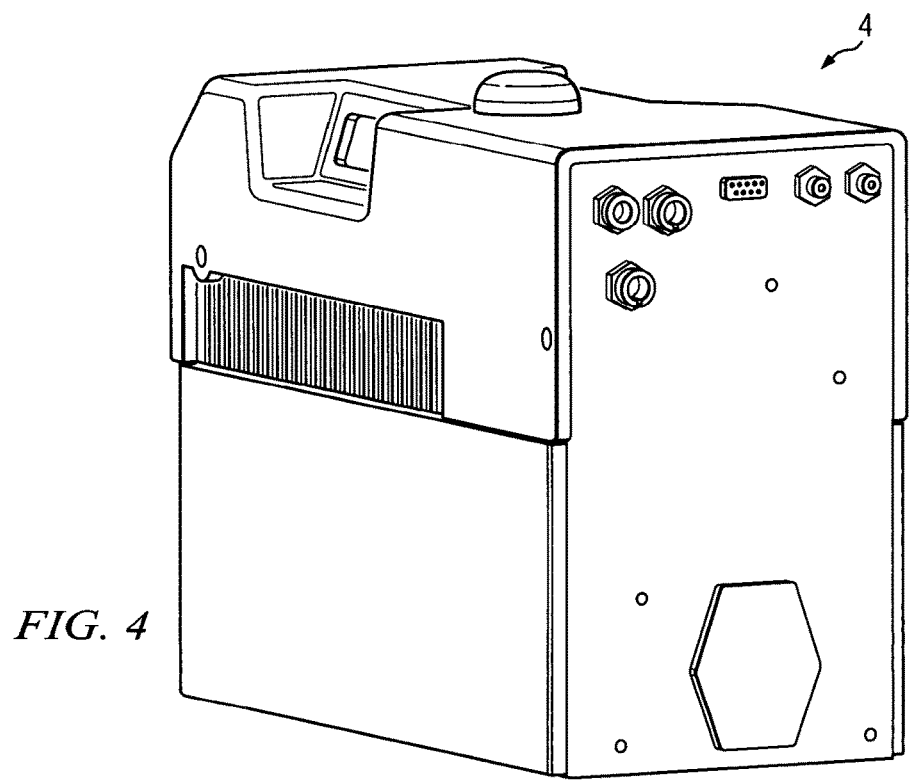
FIG. 4 is a rearwardly oriented, perspective view of the system of FIG. 1.

Referring now to FIG. 4, there is shown a rearward-oriented perspective view of the control unit 4 illustrating the connectors and couplings on the rear panel of the control unit 4 as provided for the functionality described herein. In this particular view, it may be seen that a single air connector is provided for pressurization of the blankets as described below. Likewise, a pair of fluid connectors are provided in that the fluid flow requires an outward bound and an inward bound flow of fluid to the fluid reservoir for thermal control. Likewise, the DVT connectors are provided in a pair, although a single DVT connector is used for each DVT pad. The DVT pads are pressurized in accordance with the medical modality described herein and the parameters are set by the programming within the control boards of the control unit 4. Also shown in the figure is an RS232 connector for data communication with the control unit 4. Other connections are contemplated by the Applicants such as, for example, a USB connection or a wireless connection.

Figure 5:
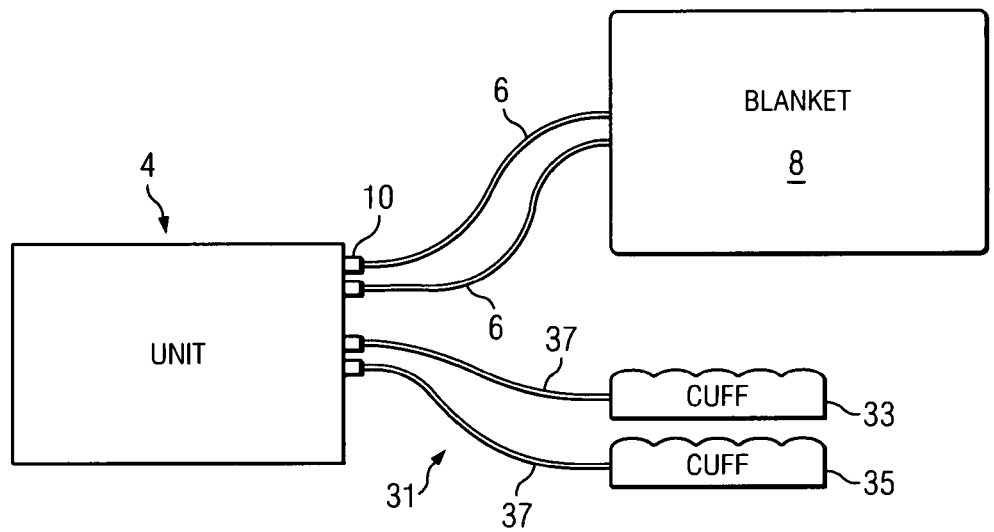
FIG. 5 is a diagrammatic schematic of the system of FIG. 1, illustrating integration of thermal and compression elements therewith.

Referring now to FIG. 5, there is shown a thermal compression-control system for thermal compression therapy wherein the control unit 4 is coupled to a thermal blanket 8 by connector tubes 6 coupled to the control unit 4 through a connector 10. The DVT prevention aspect is provided through a cuff system 31 comprising cuffs 33 and 35 that allow placement on the feet or other select regions of a patient for the DVT treatment thereof. The cuffs 33 and 35 are coupled to the control unit 4 through connector tubes 37.

Relative to the DVT pulsing, various embodiments of the present invention provide for a broad pulse configuration. It has been reported that a narrow pulse generated by opening a solenoid on compressed air may be hazardous due to the intensity of the pulse damaging cells. A broader pulse as described herein will apparently not cause the same degree of harm and may reduce harm while maintaining the same degree of efficiency in the DVT prevention. The other solenoids shown herein permit choosing between the right or left routing of the compression stroke as further defined in other figures.

Referring back to FIG. 5, it may be seen that the connector tubes 37 are mounted to the DVT connectors shown on the rear panel of the control unit 4 wherein each may provide a pressurized air in accordance with a pre-programmed application that maximizes the effectiveness of the DVT prophylaxis. In accordance with principles of the present invention, one activation technique is a high pressure low ramp-up sequence wherein the select pressure for DVT prevention is provided without a high pulse rate. It has been found by the Applicants that a high pulse rate time has been reported to create in part cell damage and it is advantageous in such a DVT prevention system to modify the conventional pulse rate to reduce cell damage. In this manner, the control boards of the control unit 4 provide a select pressurization in utilization with the solenoids shown mounted within the DVT system to carefully control the pulse ramp time in accordance with maximum medical treatment of the patient pursuant to medical concerns for such treatment.

compression in step 835. The condition of the patient is monitored in step 837 and the control parameters are adjusted in step 839 for further monitoring of the patient. Adjustments in step 839 follow monitoring the patient in step 837 as long as the system is in operation.

Figure 7:
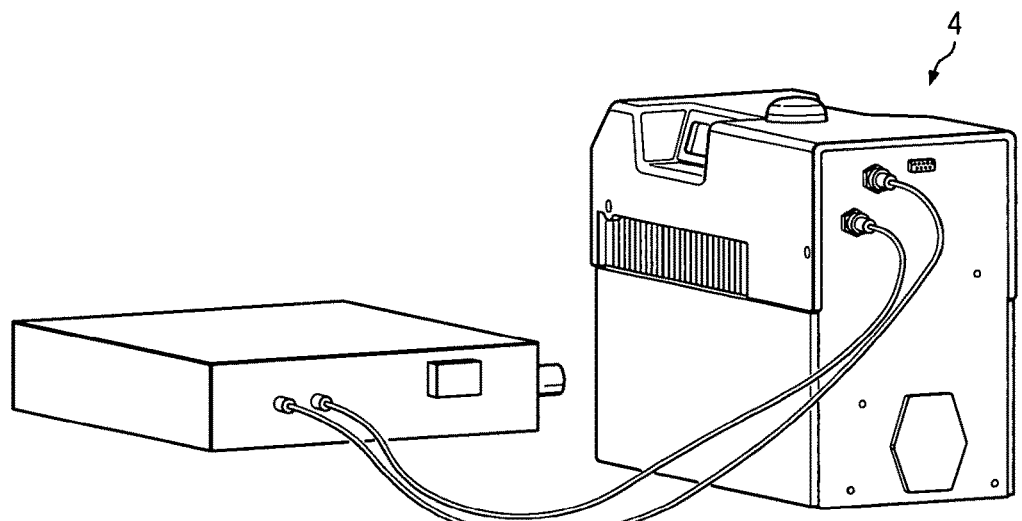
FIGS. 7-10 illustrate various embodiments of the present invention.
Figure 8:
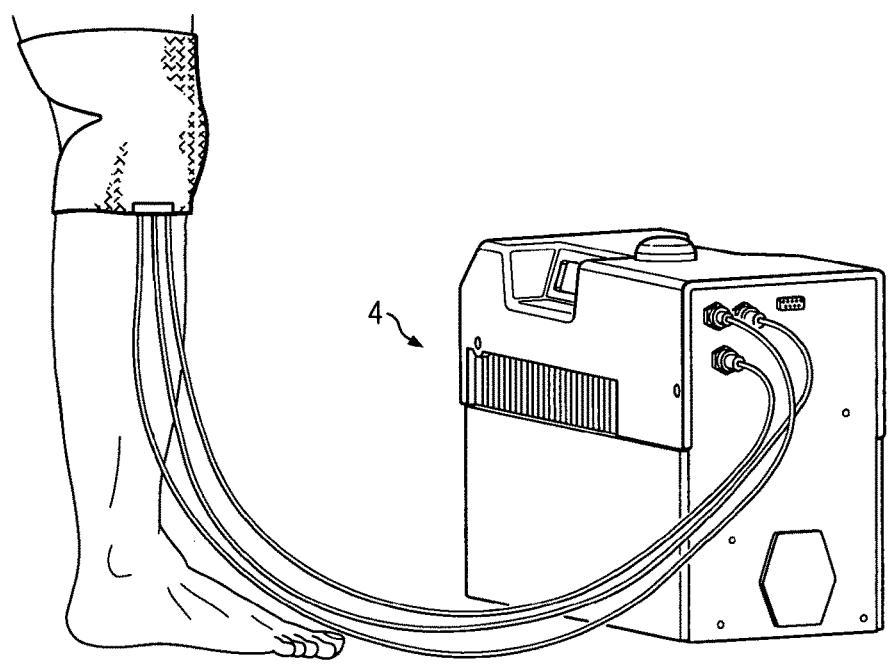

Referring now to FIGS. 7-10 together, each shows an application of an embodiment of the present invention. In FIG. 7, an industrial example is illustrated wherein a cooling umbilical is provided from control unit 4, which cooling umbilical may be utilized to cool electronic equipment as therein illustrated. Likewise in FIG. 8, the control unit 4 is shown to be connected with three tubes to provide a cooling umbilical for an individual having thermal therapy therewith. The cooling umbilical is also connected with an air line that allows an inflation of the particular wrap shown around the user's knee in this particular view for purposes of applying pressure thereagainst. This particular thermal therapy wrap or blanket will be illustrated in more detail below.

Figure 9:
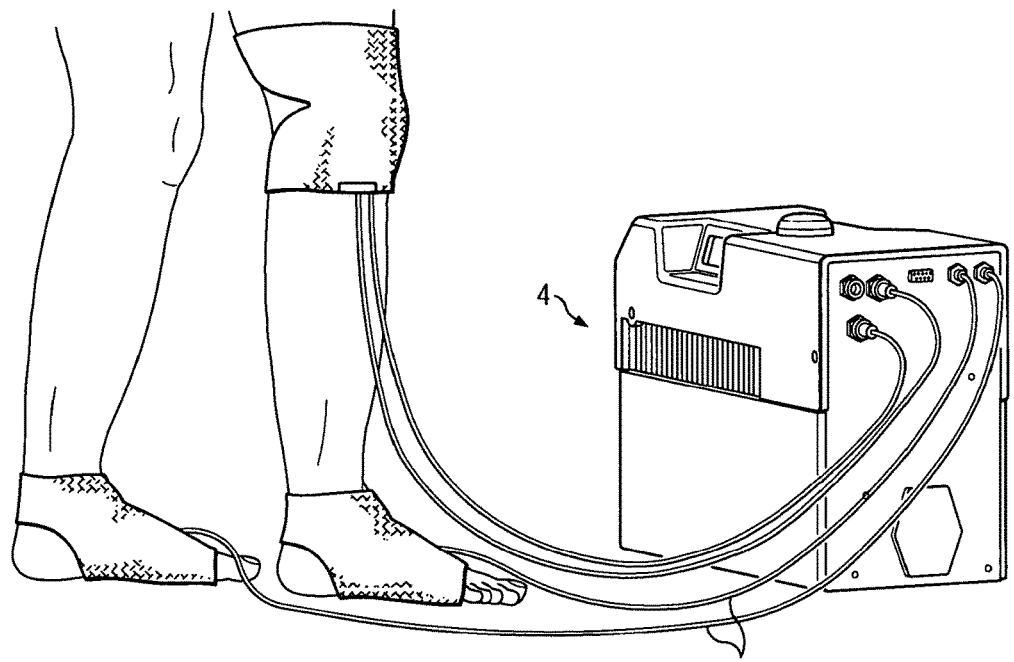

Referring now to FIG. 9, there is shown utilization of the control unit 4, wherein a cooling umbilical is utilized without any compression and DVT compression is provided

TABLE 1

| Application | Source | Mode | Pressure, mmHg | Deflation Pressure, mmHG | Inflation Time, s | Hold Time, s | Cycle Time, s | Comments |
|---|---|---|---|---|---|---|---|---|
| Calf | Literature | Both | 30-80 | 0 | 3-20 | 1-5 | 30-80 | Predominantly alternating with some simultaneous |
| | Existing Product | Alternating | ~45 | 0 | Inc. | 12 | 60 | Calf and Foot |
| | ThermoTek | Alternating | 45 | 15 | 8 | 1-5 | | Additional solenoid, line, and Colder connector |
| Foot | Literature | Alternating | 45-180 | 0 | 0.3-5 | 1-5 | 20-60 | Predominantly higher pressures; 3 sec "std" |
| | Existing Product | Alternating | 120-180 | 0 | 0.3 | 1-5 | 20-60 | |
| | ThermoTek | Alternating | 120 | 15 | 9 | 2-5 | 30 | Additional air pump, line, and fitting |

Table 1 illustrates information regarding an embodiment of the invention relative to various existing products on the market for addressing calf and foot DVT concerns. All pressure references in Table 1 pertain to mmHg above the ambient atmospheric pressure. It will be seen from Table 1 that currently available literature indicates an inflation time of 3-20 seconds for a calf and around 0.3 seconds for a foot. Such inflation times are different than those typically used by the Applicants and Applicants' assignee "ThermoTek" as referenced in Table 1 wherein the inflation time for one embodiment of the system of the present invention is on the order of 8 seconds for a calf in an alternating mode. Likewise, relative to the foot, which is often specifically of concern, an inflation time on the order of 9 seconds as compared to existing literature and existing information regarding a commercially available product in the range of 0.3 seconds. This differential is, as referenced above, a much more gradual pulse rate and is currently understood by Applicants to create less cell damage for DVT treatment. The information presented above includes preferred ranges while other times are contemplated by the Applicants to be capable of achieving the desired results.

Figure 6:
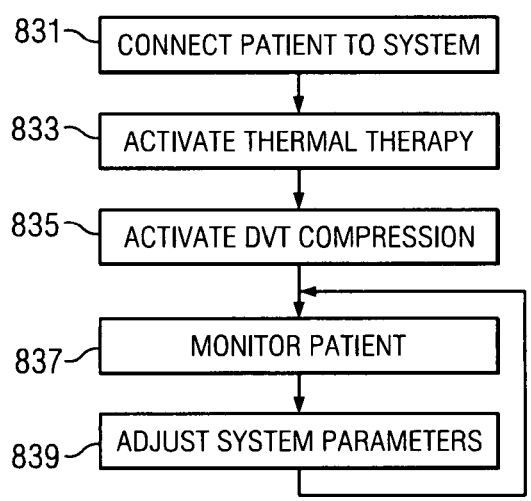
FIG. 6 is a flow diagram illustrating a thermal therapy and DVT compression process.
Figure 10:
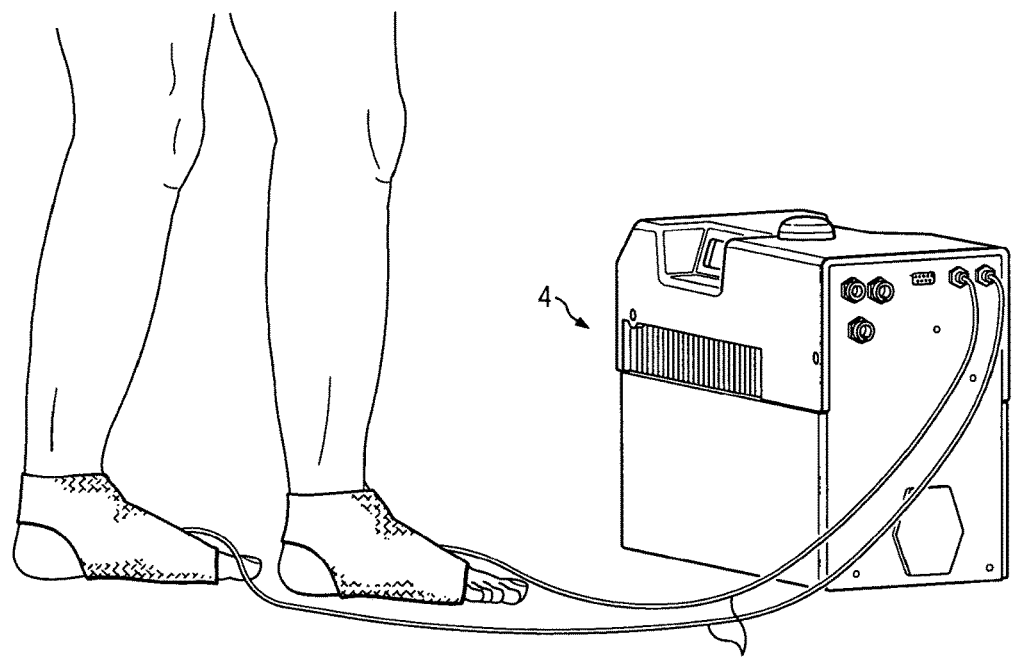

Referring now to FIG. 6, there is shown a flow diagram illustrating one embodiment of the present invention wherein the patient is initially connected to the system of control unit 4 in step 831. Next, the control unit 4 is activated for thermal therapy in step 833 and activated for DVT for both feet or calves of a patient to illustrate DVT and thermal therapy usage. In FIG. 10, only DVT is being utilized from the control unit 4 as no thermal therapy umbilicals are therein utilized.

Referring now to FIG. 11A, there is shown a DVT flat foot blanket layout 1100 of the type that may be used in accordance with the principles of the present invention. Because of the generic shape of the flat foot blanket layout 1100, a foot wrap based on the layout 1100 may be used on either a left or right foot. It may be understood that a variety of blanket layouts may be utilized for the foot during DVT treatment. It is thought that these illustrations as depicted in FIGS. 7-11 will further facilitate an understanding of principles of the present invention and enable one skilled in the art to practice same in conjunction with the control unit 4 as described herein.

Referring now to FIGS. 11B-11C, there is shown a contoured foot wrap 1104. The foot wrap 1104 is formed from a first sheet of biocompatible material 1102 and a second sheet of biocompatible material 1116 that are sealed together at sealed edge 1110. The first sheet of biocompatible material 1102 and the second sheet of biocompatible material 1116 include the front and back of the foot wrap 1104, respectively. The foot wrap 1104 includes an upper air-tight inflatable portion 1106 and a lower air-tight inflatable portion 1108. The lower air-tight inflatable portion 1108 also includes flaps 1114 and 1116. In various embodiments, flap 1114 and the upper air-tight inflatable portion 1106 include a hook-and-loop fastener hook sealed or sewn onto their front sides and the back 1116 is Velcro® compatible to receive the hooks. An inlet 1116 is located on the back of the foot wrap 1116 on the lower air-tight inflatable portion 1108 to facilitate the intake and exhaust of air.

Figure 11D:
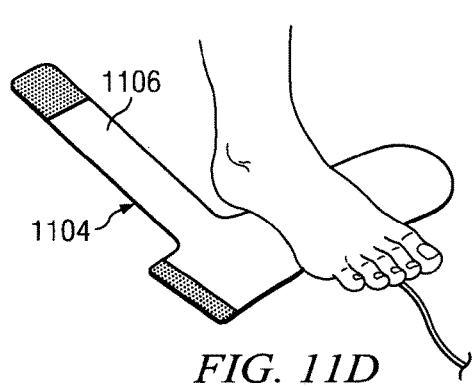
Figure 11E:
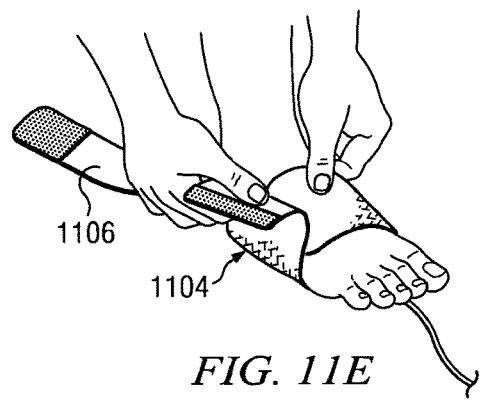
Figure 11F:
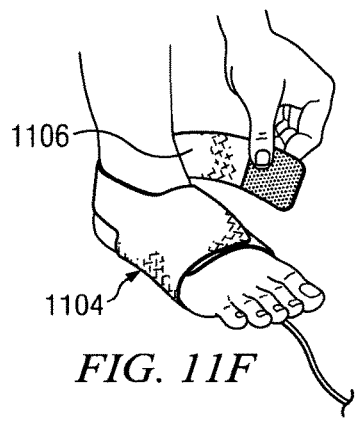
Figure 11G:
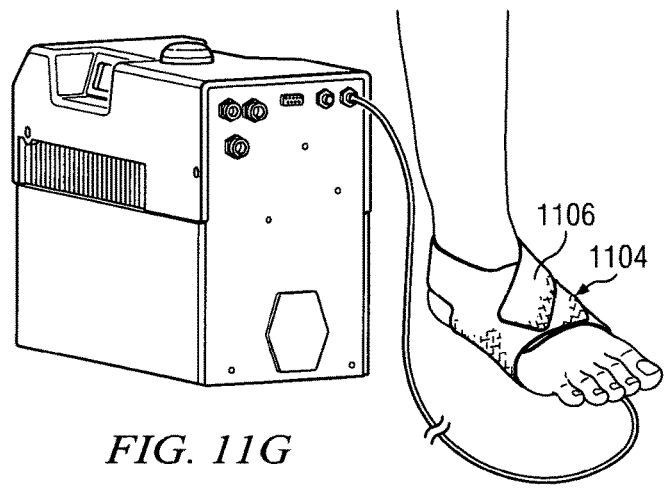

Referring now to FIGS. 11D-11G, the operation of the foot wrap 1104 is described. With reference to FIG. 11D-11E, a foot is placed into the foot wrap 1104 with the foot engaging the front side 1102 of the foot wrap 1104. With reference to FIGS. 11E-11F, the flaps are pulled tight and the foot wrap 1104 is secured. The contoured foot wrap 1104 may be now be connected to the control unit 4 via a DVT connector 37 connected to inlet 1116 for DVT therapy according to the present invention, as depicted in FIG. 11G.

Figure 18A:
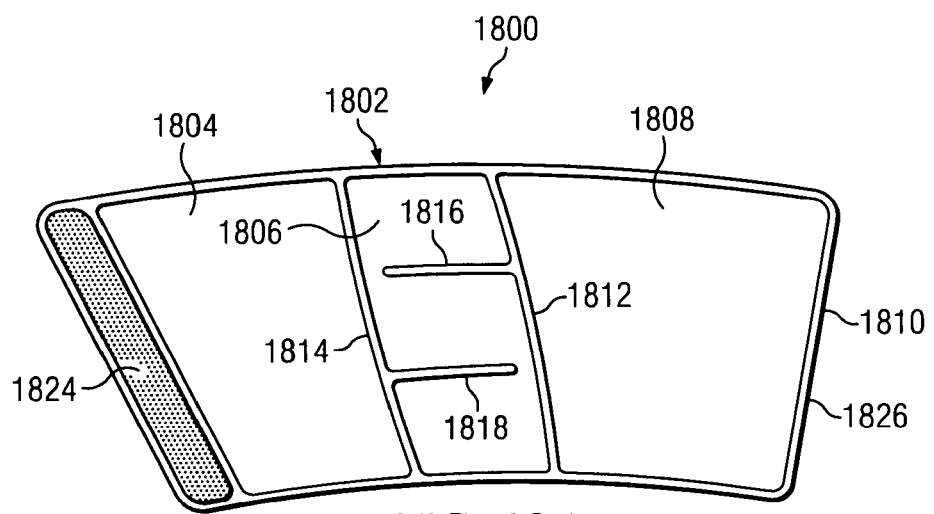
FIGS. 18A-18D illustrate a DVT calf wrap.
Figure 18B:
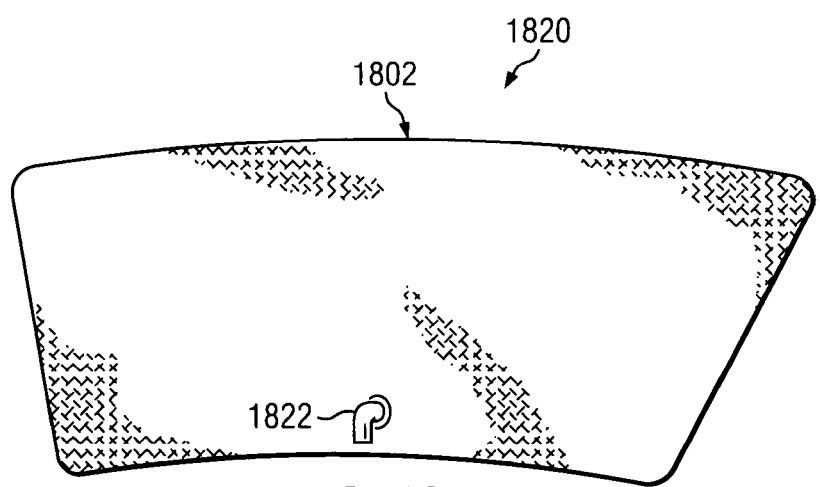

Referring now to FIGS. 18A-18B, there is shown a trapezoidal DVT calf blanket 1802 of the type that may be used in accordance with principles of the present invention. As with the flat foot blanket layout, a variety of blanket layouts may be used for the calf during DVT treatment. A calf wrap 1802 is formed of two sheets of biocompatible material 1800 and 1820, including the front and back of the calf wrap 1802, respectively. The front 1800 and back 1820 are sealed or sewn together at a sealed edge 1810. Additionally, the calf wrap is divided into three chambers (1804, 1806, and 1808) by welds 1812 and 1814. The middle chamber 1806 is characterized by two additional welds 1816 and 1818. Weld 1816 extends from weld 1812 and weld 1818 extends from weld 1814, creating an 'S' shaped chamber. The three-chamber structure as described herein permits a compression gradient across the three chambers. In various embodiments, all welding may be accomplished by radio frequency (RF) welding. The front side 1800 also includes flaps 1824 and 1810. In various embodiments, flap 1824 may have sealed or sewn thereon a Velcro® hook and back side 1820 may be Velcro® compatible to receive the hook. An inlet 1822 is located on the back of the calf wrap 1802 to facilitate the intake and exhaust of air.

Figure 18C:
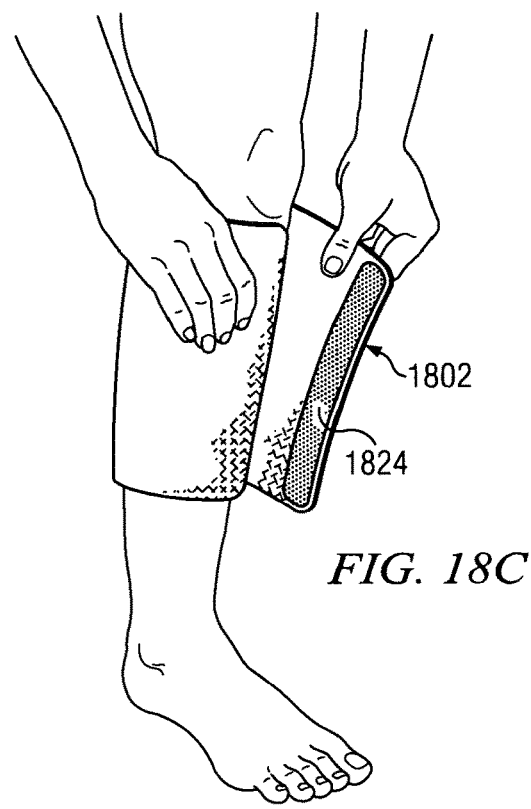
Figure 18D:
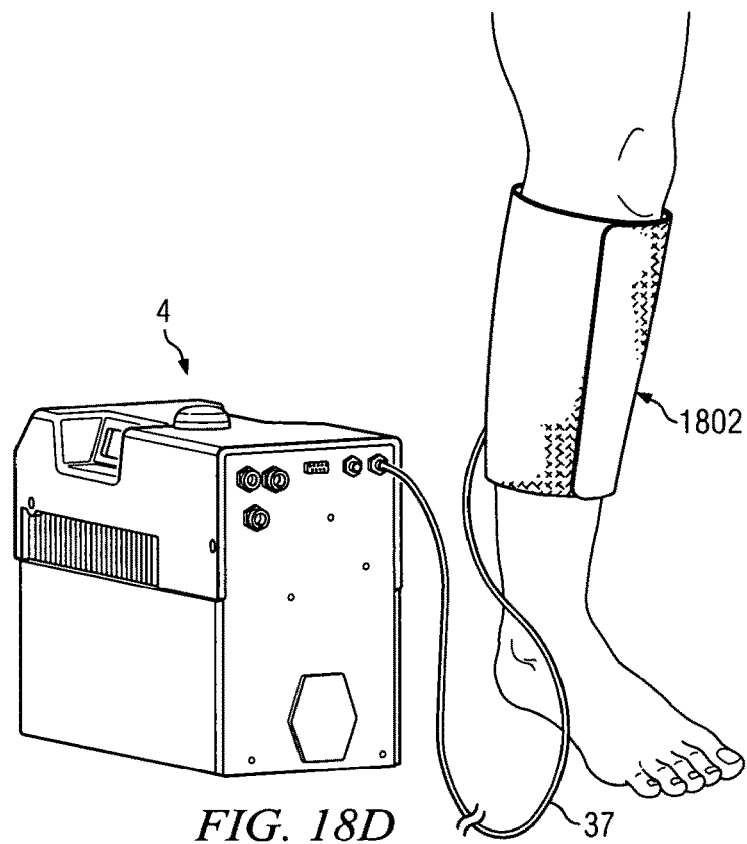

Referring now to FIGS. 18C-18D, operation of the calf wrap 1802 is described. With reference to FIG. 18C, the calf wrap 1802 is positioned on the front side of the calf. Flap 1826 is pulled tight and then flap 1824 is pulled tight overtop and attached. With reference to FIG. 18D, the calf wrap may be connected to the control unit 4 for DVT therapy according to the present invention by connecting DVT connector 37 to inlet 1822.

Figure 12:
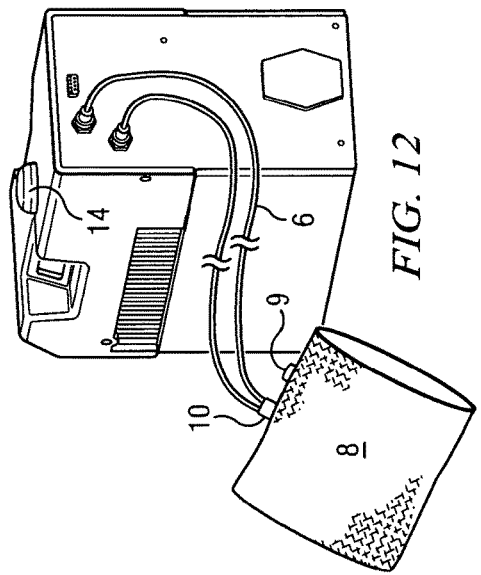
FIG. 12 is a schematic illustrating utilization of one embodiment of the control unit with a more detailed illustration of a thermal therapy blanket.

Referring now to FIG. 12, there is shown a thermal therapy application without pressure applied (similar to the thermal therapy illustrated in FIG. 9). As shown herein, heat transfer fluid flows into the blanket 8 through an inlet port, and exits through an outlet port to the control unit 4 via the connector 10 and connector tubes 6. Gas may be pumped by the control unit 4 to the blanket 8 through the connector tubes 6 and the connector 10 to provide compression (not shown in this view). While the embodiment described above pumps gas to provide compression, it is also contemplated that other substances could be utilized to provide the desired compression.

The control unit 4 and the blanket 8 may be adapted for the administration of hot, cold, and/or compression therapies to a body portion of the patient. For example, the blanket 8 may cover different areas of the human body. Current thermal design requirements for temperature therapy in various embodiments of the present invention are as follows: 1) the system must be able to heat the fluid from around 49° F. to around 105° F. with the largest blanket attached to a typical man (e.g., 5'10" and 180 lbs.) at an ambient of 77° F. within 10 minutes; 2) the system must be able to cool the fluid from 105° F. to 49° F. with the largest blanket attached to the typical man at an ambient of 77° F. within 20 minutes; and 3) the system must cool the fluid to 37° F. at an ambient of 77° F. within 90 minutes. These requirements should be with a minimum compression of 25 mm Hg. The connector 10 provides a fluid and/or gas connection between the control unit 4 and the blanket 8 for the transfer of gas and heat transfer fluid. The connector 10 may also allow for transfer of electrical sensor signals and/or data signals between the blanket 8 and the control unit 4. The emergency relief valve 9 is utilized to quickly decompress the blanket 8 if needed.

Figure 13A:
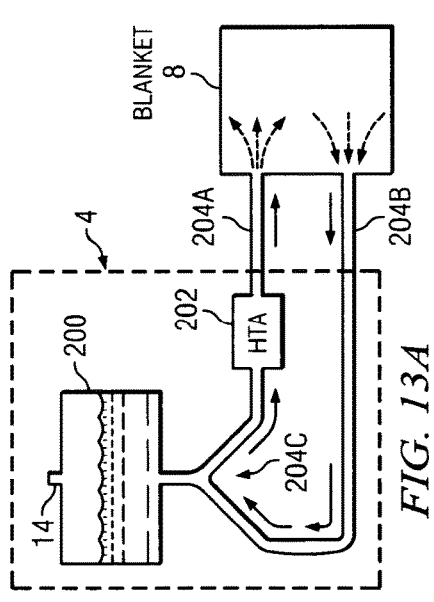
FIG. 13A is a flow diagram of one aspect of the thermal operation of the thermal therapy system as represented in FIG. 12.

Referring now to FIG. 13A, a block diagram of one embodiment of the flow of heat transfer fluid between the control unit 4 and the blanket 8 is illustrated. The control unit 4 includes a heat transfer fluid reservoir 200 and at least one heat transfer assembly (HTA) 202 for heating and/or cooling the heat transfer fluid. Before the blanket 8 is utilized for temperature therapy, the system is primed with the heat transfer fluid. When the system is primed, substantially no air exists in the tubes 204 between the reservoir 200, HTA 202, and blanket 8. The flow tubes in the control unit 4 between the reservoir 200, HTA 202, and blanket 8 form a three-point junction 204C. In embodiment, the three-point junction 204C is formed as an inverted Y, however, other shapes and orientations are possible. By utilizing a three-point junction 204C, the heat transfer fluid returning from the blanket 8 is recirculated to the HTA 202 without utilizing heat transfer fluid from the reservoir 200. The three-point junction 204C allows the HTA 202 to heat or cool the heat transfer fluid that has already been heated or cooled prior to entering the blanket 8. In the preferred embodiment, the HTA 202 does not heat or cool the entire contents of the reservoir 200, but merely the portion of the heat transfer fluid that is currently circulating through the blanket 8 and tubing 204. The reservoir is typically by-passed unless more fluid volume is needed. In the three-point junction 204C, heat transfer fluid returning from the blanket 8 may be pulled, via a pump, to the HTA 202. If more heat transfer fluid than that which is already circulating through the system is required, then the heat transfer fluid from the reservoir is introduced into the system.

Figure 13C:
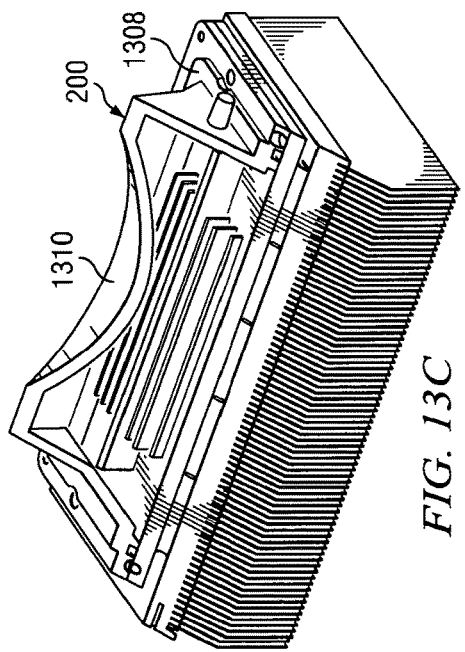
FIG. 13C is a perspective view of an integrated reservoir and HTA according to a preferred embodiment of the present invention.
Figure 13B:
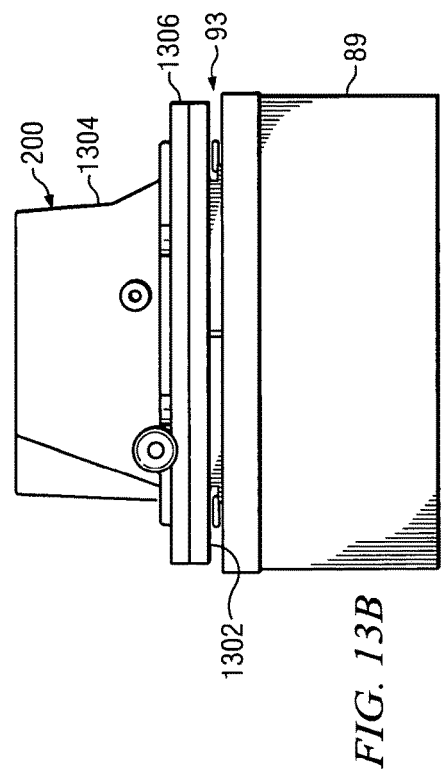
FIG. 13B is a rear view of an integrated reservoir and heat transfer assembly (HTA)

Referring now to FIGS. 13B-13C, the integration of the reservoir 200 and the HTA 202 is illustrated. With reference to FIG. 13B, the rear of the reservoir 200 includes a coolant supply port 1302 for supplying heat transfer fluid to the fluid pump 91, a coolant return port 1304 for receiving heat transfer fluid from the blanket 8, and a cold plate 1306. The cold plate 1306 is positioned at the base of the reservoir 200 and is therefore in direct contact on its underside with the TEC 93. Referring now specifically to FIG. 13C, a divider 1308 is located in the middle of the reservoir 200 between the coolant supply port 1302 and the coolant return port 1304, thereby blocking direct flow of fluid between the two ports. As fluid flows into the back of the reservoir 200 through the coolant return port 1304, the divider 1308 channels the fluid to the front of the reservoir 200 and then back to the coolant supply port 1302. By preventing fluid from short circuiting directly from the coolant return port 1304 to the coolant supply port 1302, the divider 1308 forces exposure of the fluid to the cold plate 1306 which, as a result of its direct contact with the TEC 93, provides a surface area to cool or heat the fluid. The reservoir 200 also includes vertical fins 1310 to further enhance contact areas with the fluid. In one preferred embodiment, the vertical fins are spaced 0.5 inches apart and span the length of the reservoir 200.

Figure 14:
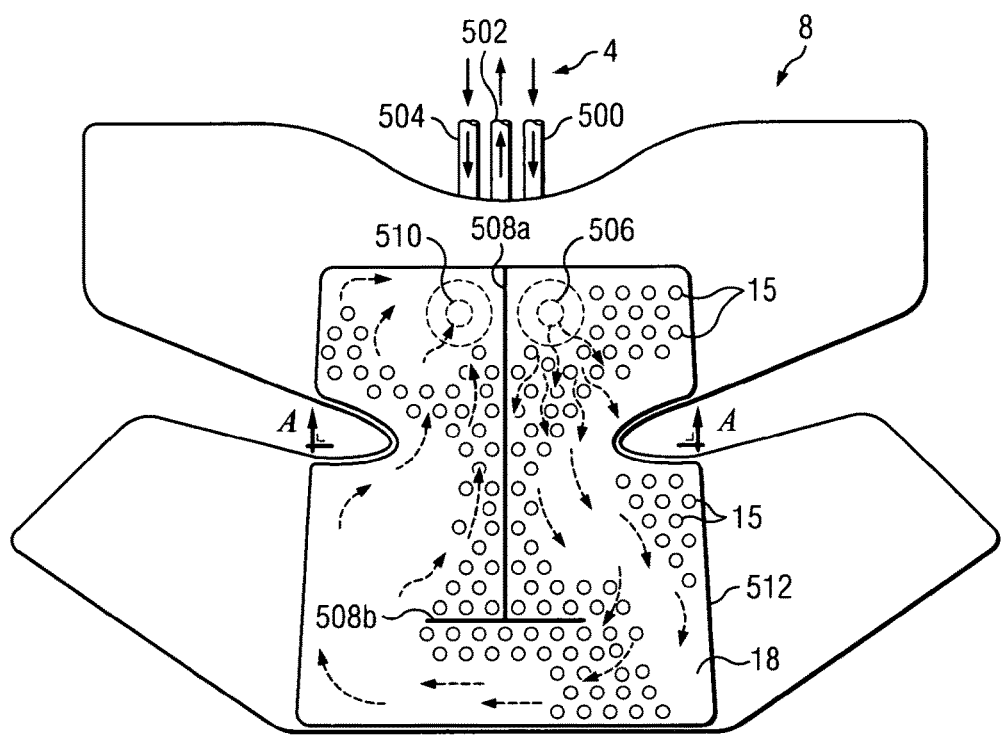
FIG. 14 is a plan view of an embodiment of a thermal therapy blanket.

Referring now to FIG. 14, a temperature therapy blanket 8 having a pre-selected shape and compression capabilities is illustrated. The underside of the blanket 8 (shown) is placed directly against a portion of the patient. The fluid bladder is thus adjacent to the patient. Heat transfer fluid flows into the blanket 8 from inlet hose 500 and heat transfer fluid flows out of the blanket via outlet hose 502. A gas for compression flows into the blanket 8 from air inlet hose 504. Heat transfer fluid travels through the inlet hose 500, through fluid inlet port 506, and into the blanket 8. The connections 15 allow the heat transfer fluid to more evenly disperse throughout the fluid bladder. Partitions 508a, 508b control the flow of heat transfer fluid throughout the fluid bladder. Partition 508a prevents heat transfer fluid from entering the blanket 8 at the inlet port 506 and immediately exiting the blanket via outlet port 510. Partition 508a forces the heat transfer fluid to travel towards the end of the blanket 8 remote from the inlet port 506. Partition 508b, in conjunction with connections 15, causes the heat transfer fluid to travel across the width of the blanket 8. The edges of the fluid bladder are joined to the edges of the air bladder at seal 512. The heat transfer fluid may then exit the blanket 8 at the outlet port 510. The travel of the heat transfer fluid is indicated by arrows.

Figure 15:
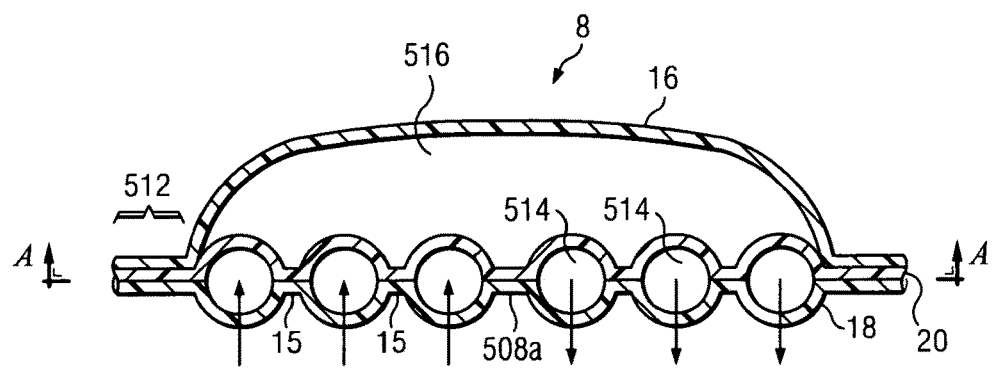
FIG. 15 is a cross-sectional view of the blanket of FIG. 14 illustrating flow of thermal fluid therein and utilization of compression air thereabove for use in achieving a compression of the thermal fluid against the skin of a patient.
Figure 19:
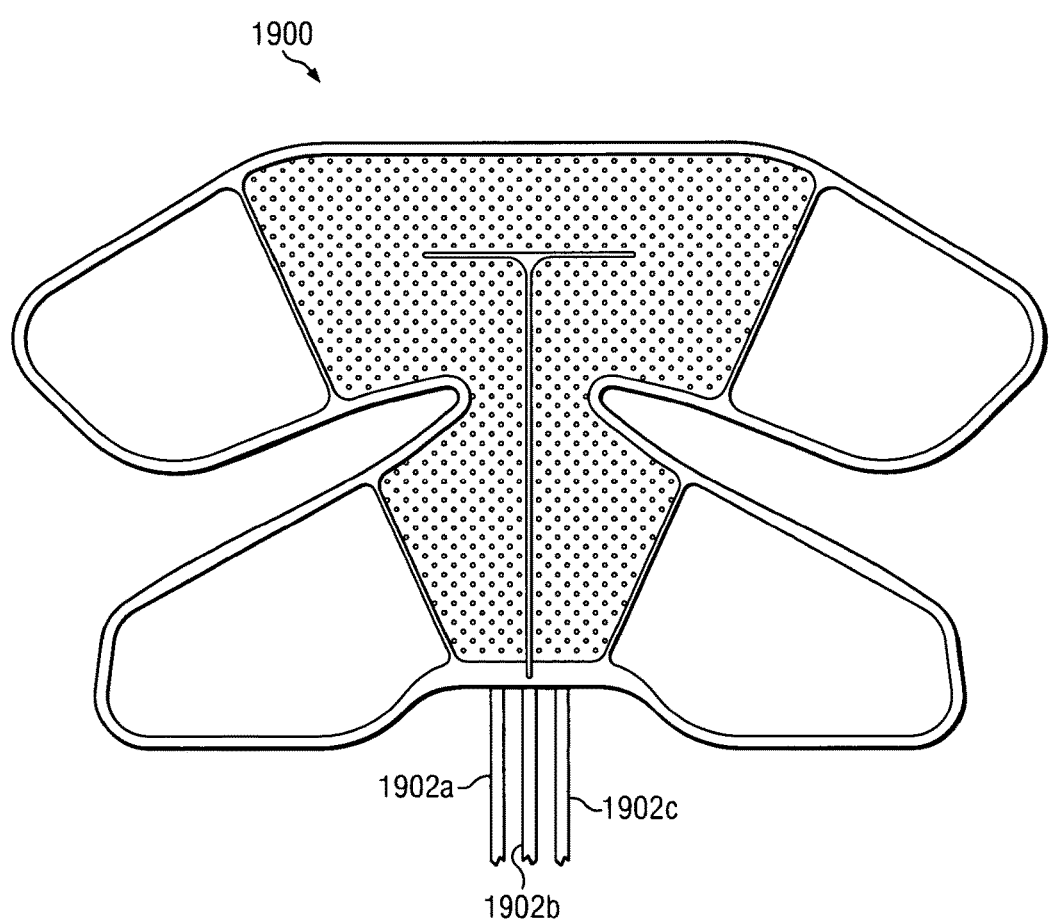
FIG. 19 is a plan view of an embodiment of a thermal therapy blanket.

Referring now to FIG. 15, the blanket 8 is turned over relative to FIG. 14 and a cross-sectional view along line A-A of FIG. 14 is illustrated. As described above, the fluid bladder 514 (disposed against the patient) and the air bladder 516 are joined together at seal 512. Connections 15 join the upper layer and lower layer of the fluid bladder 514 together. The partition 508a segregates the heat transfer fluid from the inlet port 506, illustrated by downward arrows, from the heat transfer fluid flowing to the outlet port, illustrated by the upward arrows. The air bladder 516 is oriented over the fluid bladder 514 and serves to press the fluid bladder 514 against a portion of the patient (not shown in this view). In another embodiment, the fluid bladder 514 and the air bladder 516 may have low-profile inline ports such as inline ports 1902(a)-(c) of a temperature therapy blanket 1900 of FIG. 19. Inline ports afford increased comfort to a user by allowing the blanket 8 to lay substantially flat. The embodiment shown allows users to sleep or rest while using the blanket 8.

Figure 16:
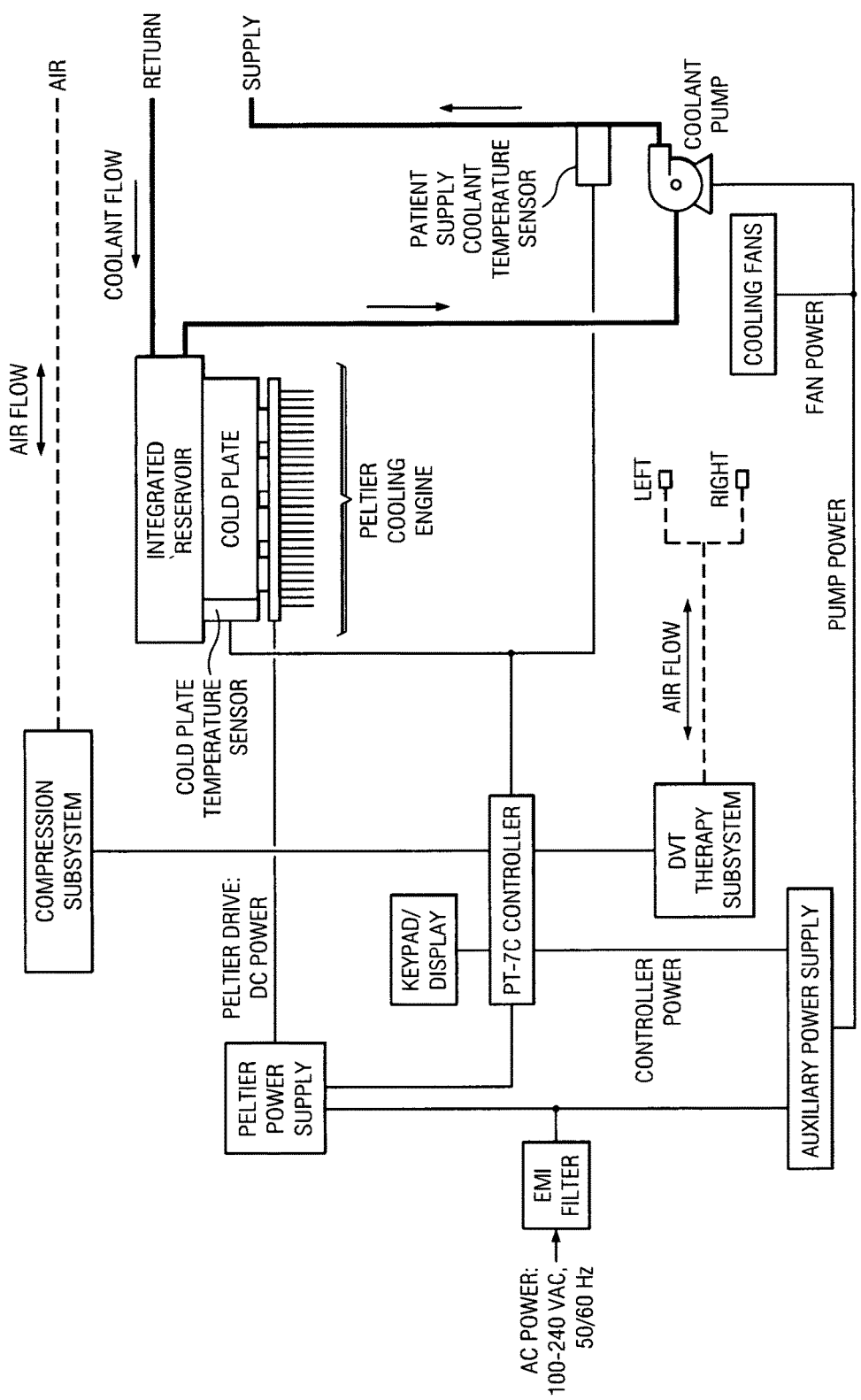
FIG. 16 is a thermal therapy/DVT system block diagram.

Referring now to FIG. 16, there is shown a thermal therapy/DVT system block diagram where air is provided in a compression subsystem in conjunction with Peltier cooling of a fluid for thermal therapy. The coolant flow is thermally conditioned by the Peltier cooling engine. Patient supply cooling temperature sensors are utilized in conjunction therewith. Coolant pumps are utilized in conjunction with cooling fans. The cooling fans, as described above, provide selective cooling in a manner most efficient for the construction and operation of the control unit 4. In that regard, FIG. 16 may be utilized in understanding various aspects of operation of the system of the present invention as further defined below.

Various of the above-described Figures illustrate the mounting of dual-fan assemblies for impinging style airflow. In this manner, the air is brought in at the base of the heat sink and driven in or impinged against the heat sink, which serves to lower the pressure drop and increase air flow for a given heat sink. A single heat sink may be used. Such a configuration of air flow with an enlarged grate configuration may be used to afford noise abatement.

In one embodiment, the size of the reservoir has been reduced relative to a number of earlier models of thermoelectric (TEC) systems such that only around 175 watts are utilized compared to 205 for typical earlier systems. As such, the control unit 4 is configurable with TEC assemblies maximizing efficiency. With such an assembly, multiple applications of industrial with non-air compression and/or medical with air compression and/or DVT is afforded in a single chassis 81. With regard to the medical modality, thermal therapy may be afforded to a patient to reduce swelling and edema while, in conjunction with the DVT prophylaxis, preventing blood from pooling in lower body extremities. This is particularly important after surgery when anesthesia has been involved. It is well known that anesthetics often tend to reduce the wall strength of veins and, if not otherwise treated, appropriate venous pumping may not be afforded allowing for blood pooling in clots. With the DVT application as disclosed herein, both thermal and DVT prophylaxis with a low-noise configuration may be achieved.

Still referring to FIG. 16, the Peltier power supply is shown to be controlled by a pt-7c controller accessed via a keypad display. Various other features for control and power supply have likewise been included, such as an electromagnetic interference (EMI) filter and auxiliary power supply used in conjunction with the DVT therapy subsystem. It may be seen that the DVT therapy subsystem provides a separate airflow for both left and right applications that were described above for utilization in the DVT treatment of a patient illustrated in FIGS. 9 and 10.

For purposes of this patent application, the following definitions are to be used:
hot: >15° C. greater than ambient temperature;
cold: <15° C. less than ambient temperature;
about: not more than 10% more or less than stated value;
around: not more than 10% more or less than stated value; and
biocompatible: referring to a material that the body generally accepts without a significant immune response.

Figure 17:
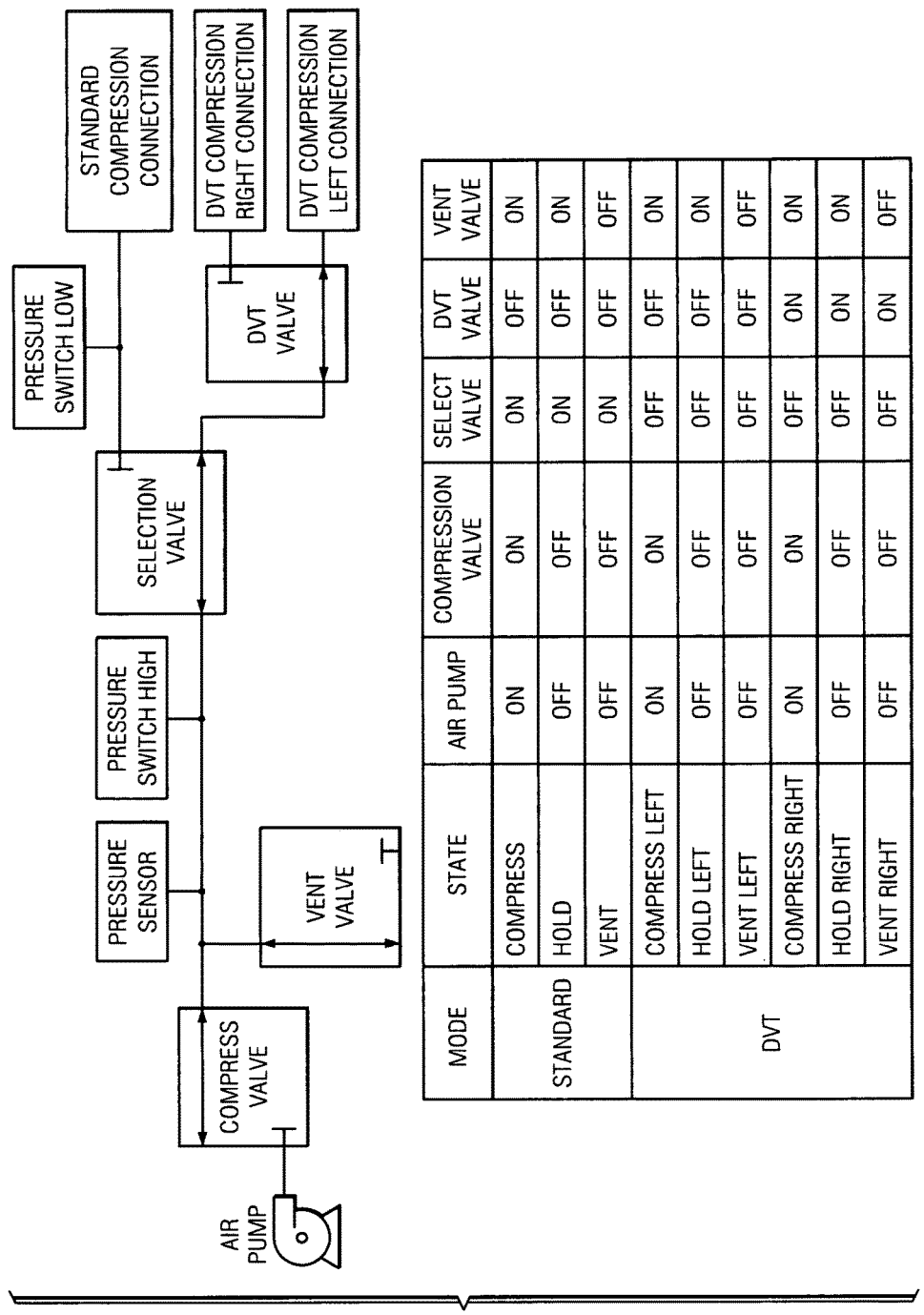
FIG. 17 is a DVT therapy block diagram further illustrating the operation thereof.

Referring now to FIG. 17, there is shown a DVT therapy block diagram where the air pump is shown to be in flow communication with a compress valve utilized with a vent valve and a pressure sensor in association with a pressure switch high and pressure switch low. This DVT therapy block diagram is provided to further facilitate an understanding of the DVT therapy provided by the control unit 4 in accordance with various embodiments of the present invention when DVT compression is provided from two outlets of the control unit 4. The various modes of operation utilizing air pump, compression valve, select valve, DVT valve, and vent valve are shown.

The previous description is of embodiments of the invention. The scope of the invention should not necessarily be limited by this description. The scope of the present invention is instead defined by the following claims.

What is claimed is:
1. A combination thermal compression method for deep vein thrombosis therapy, the method comprising:
thermally conditioning, via a control unit, a fluid to a predetermined temperature;
providing the fluid to a thermal blanket via a hose;
returning the fluid to the control unit via the hose;
securing the thermal blanket to an extremity of a patient, wherein the thermal blanket is integrated with a first compression device and the first compression device is disposed outwardly of the thermal blanket;

securing a second compression device to the extremity of the patient at a location distal to the thermal blanket;

providing, via a compression subsystem in the control unit, compressed gas to the first compression device to compress the thermal blanket against the extremity so as to deliver a first treatment modality to the extremity;

applying, via a DVT therapy subsystem in the control unit, pulsed compression therapy treatment to at least the extremity via the second compression device so as to deliver a second treatment modality to the patient; and wherein the control unit automatically directs compressed air alternately to the first compression device and the second compression device such that the first treatment modality and the second treatment modality are delivered to the extremity in an alternating fashion.

2. The method of claim 1, wherein compressed gas is directed first to the first compression device before being directed to the second compression device.

3. The method of claim 1, wherein the compressed gas is directed first to the second compression device before being directed to the first compression device.

4. The method of claim 1, wherein the conditioning comprises heating the fluid from a pre-determined cold temperature to a pre-determined hot temperature and maintaining the pre-determined hot temperature for a set period of time.

5. The method of claim 1, wherein the conditioning comprises cooling the fluid from a predetermined hot temperature to a pre-determined cold temperature and maintaining the pre-determined cold temperature for a pre-determined period of time.

6. The method of claim 1, wherein the conditioning comprises alternatingly heating and cooling the fluid between pre-determined temperatures for pre-determined times.

7. The method of claim 1, wherein the providing compressed gas and the applying pulsed compression comprises generating pressures within the first compression device and the second compression device in the range of approximately 0 to approximately 120 mmHg.

8. The method of claim 1, wherein the control unit comprises a first outlet that facilitates connection of the control unit to the first compression device and a second outlet that facilitates connection of the control unit to the second compression device.

9. The method of claim 1, wherein the thermal blanket may be secured to a variety of anatomical regions of the patient.

10. The method of claim 1, wherein the providing fluid to the thermal blanket occurs simultaneously with the providing compressed gas to the first compression device.

11. The method of claim 1, comprising at least two second compression devices; and wherein pulsed compression therapy is applied to the at least two second compression devices in sequence.

12. The method of claim 1, comprising at least two second compression devices; and wherein pulsed compression therapy is applied to the at least two second compression devices simultaneously.

* * * * *